(12) United States Patent
Kim et al.

(10) Patent No.: US 10,709,793 B2
(45) Date of Patent: Jul. 14, 2020

(54) GENE/CARRIER COMPLEX FOR PREVENTING OR TREATING INFLAMMATORY DISEASES

(71) Applicants: INDUSTRY-UNIVERSITY COOPERATION FOUNDATION HANYANG UNIVERSITY, Seoul (KR); INDUSTRY-UNIVERSITY COOPERATION FOUNDATION HANYANG UNIVERSITY ERICA CAMPUS, Gyeonggi-do (KR)

(72) Inventors: Yong-Hee Kim, Seoul (KR); Tae-Hwan Kim, Seoul (KR); Chul-Su Yang, Gyeonggi-do (KR); Yoonsung Song, Gyeonggi-do (KR); Jee-Young Chung, Seoul (KR); Sungsin Jo, Gyeonggi-do (KR); So Mi Kim, Seoul (KR); Qurrat Ui Ain, Seoul (KR); Ye-Ram Kim, Daejeon (KR)

(73) Assignees: INDUSTRY-UNIVERSITY COOPERATION FOUNDATION HANYANG UNIVERSITY (KR); INDUSTRY-UNIVERSITY COOPERATION FOUNDATION HANYANG UNIVERSITY ERICA CAMPUS (KR)

( * ) Notice: Subject to any disclaimer, the term of this patent is extended or adjusted under 35 U.S.C. 154(b) by 0 days.

(21) Appl. No.: 16/179,876

(22) Filed: Nov. 2, 2018

(65) Prior Publication Data
US 2019/0054180 A1 Feb. 21, 2019

Related U.S. Application Data

(63) Continuation-in-part of application No. 15/721,199, filed on Sep. 29, 2017, now abandoned.

(30) Foreign Application Priority Data

Sep. 30, 2016 (KR) .................. 10-2016-0126284
Sep. 25, 2017 (KR) .................. 10-2017-0123413
Sep. 25, 2017 (KR) .................. 10-2017-0123414

(51) Int. Cl.
*C07H 21/04* (2006.01)
*A61K 47/62* (2017.01)
*C12N 15/113* (2010.01)
*A61K 31/7088* (2006.01)
*A61P 37/06* (2006.01)
*A61P 19/02* (2006.01)
*A61K 47/64* (2017.01)

(52) U.S. Cl.
CPC .......... *A61K 47/62* (2017.08); *A61K 31/7088* (2013.01); *A61K 47/6455* (2017.08); *A61P 19/02* (2018.01); *A61P 37/06* (2018.01); *C12N 15/1137* (2013.01); *C12Y 304/24086* (2013.01); *C12N 2310/122* (2013.01); *C12N 2310/14* (2013.01); *C12N 2310/351* (2013.01); *C12N 2310/3517* (2013.01); *C12N 2310/531* (2013.01); *C12N 2320/32* (2013.01)

(58) Field of Classification Search
None
See application file for complete search history.

(56) References Cited

FOREIGN PATENT DOCUMENTS

| KR | 1020090120948 | 5/2011 |
| KR | 1020120093306 | 8/2012 |

OTHER PUBLICATIONS

Wong, Eitan, et al. "Harnessing the natural inhibitory domain to control TNFα converting enzyme (TACE) activity in vivo." Scientific reports 6 (2016): 35598.*
Kim, So Mi, "Development of non-viral RNA interference system against TACE (Tumor necrosis factor-α converting enzyme) for the treatment of inflammatory diseases", Dept. of Bioengineering, the Graduate School, Hanyang University, Republic of Korea (2014).
Song, Yoonsung et al., "RNAi-mediated silencing of TNF-α converting enzyme to down-regulate soluble TNF-α production for treatment of acute and chronic colitis", Journal of Controlled Release 239 (2016) 231-241.

* cited by examiner

*Primary Examiner* — Kimberly Chong
(74) *Attorney, Agent, or Firm* — Adsero IP

(57) ABSTRACT

Disclosed is a gene/carrier complex for preventing or treating inflammatory diseases, including tumor necrosis factor-α converting enzyme (TNF-α converting enzyme, TACE) shRNA and a nonviral gene carrier, wherein the nonviral gene carrier includes an acetate of disulfide-linked poly(oligo-arginine) or a TFA salt of poly(oligo-aspartic acid)poly(oligo-arginine).

14 Claims, 16 Drawing Sheets
Specification includes a Sequence Listing.

[FIG. 1]
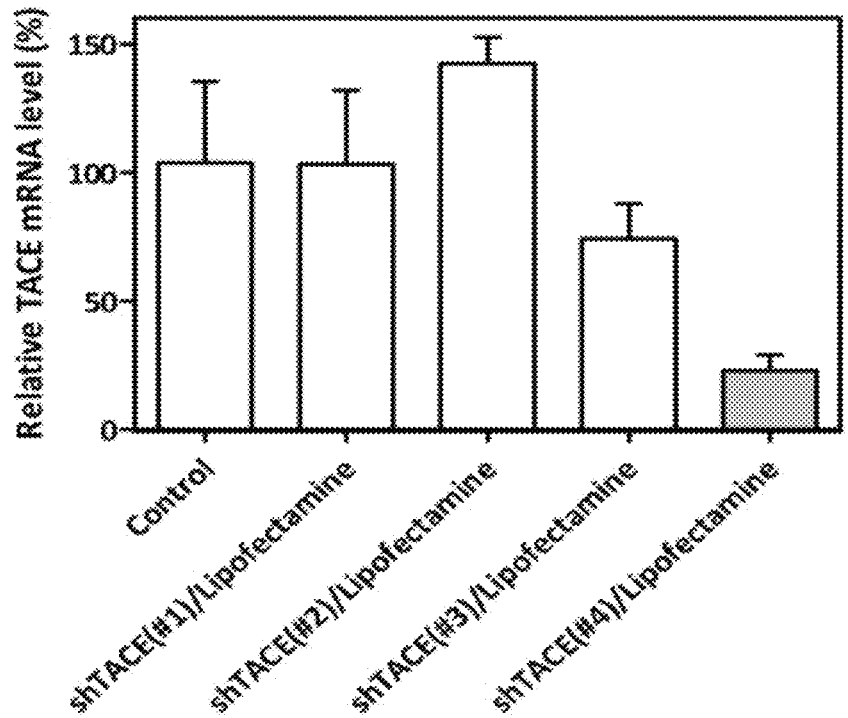
[FIG. 2]
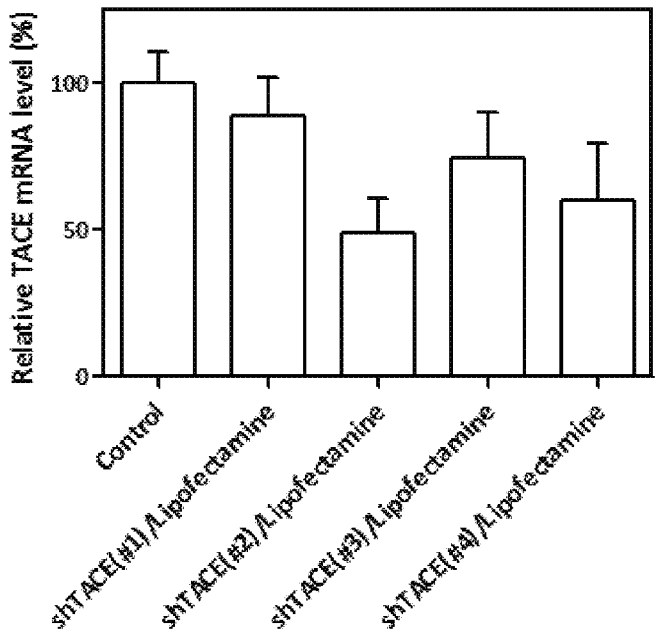

[FIG. 3]
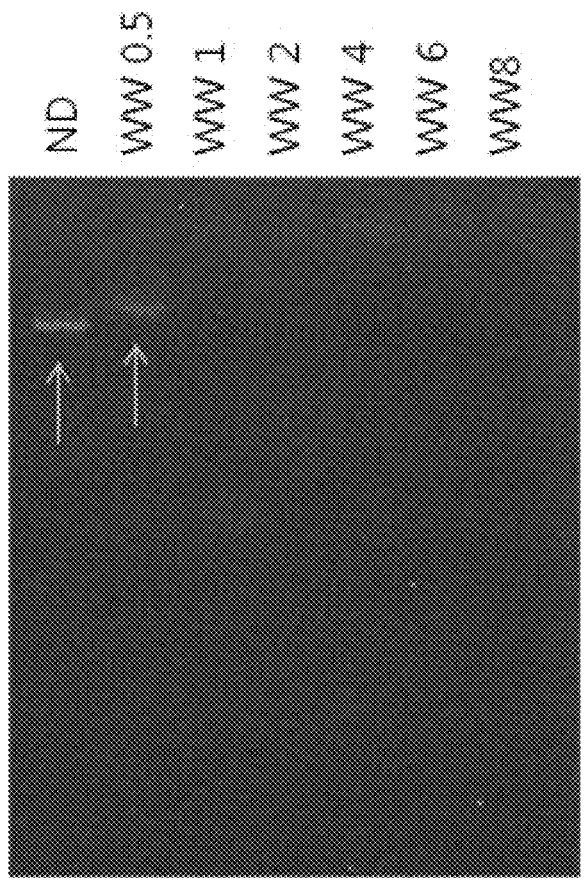
[FIG. 4]
|  | Zeta potential (mV) | Size (nm) | PDI |
|---|---|---|---|
| Average | 23.00 | 178.83 | 0.253 |
| Standard deivation | 9.65 | 33.84 | 0.075 |

[FIG. 5]
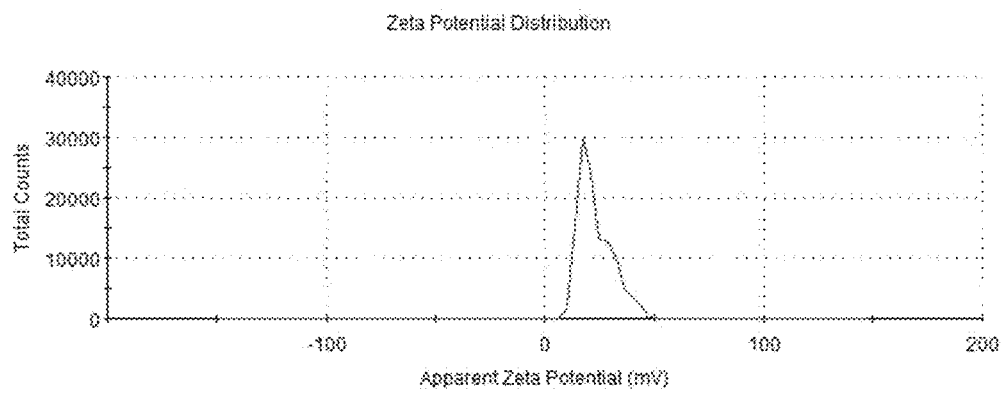
[FIG. 6]
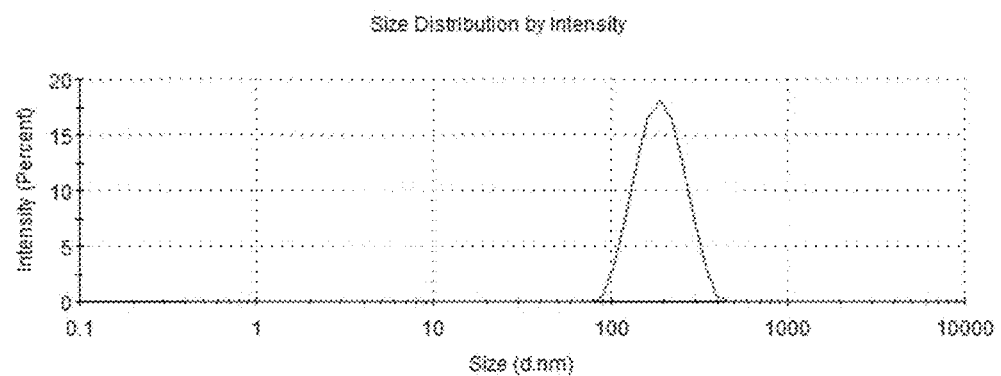
[FIG. 7]
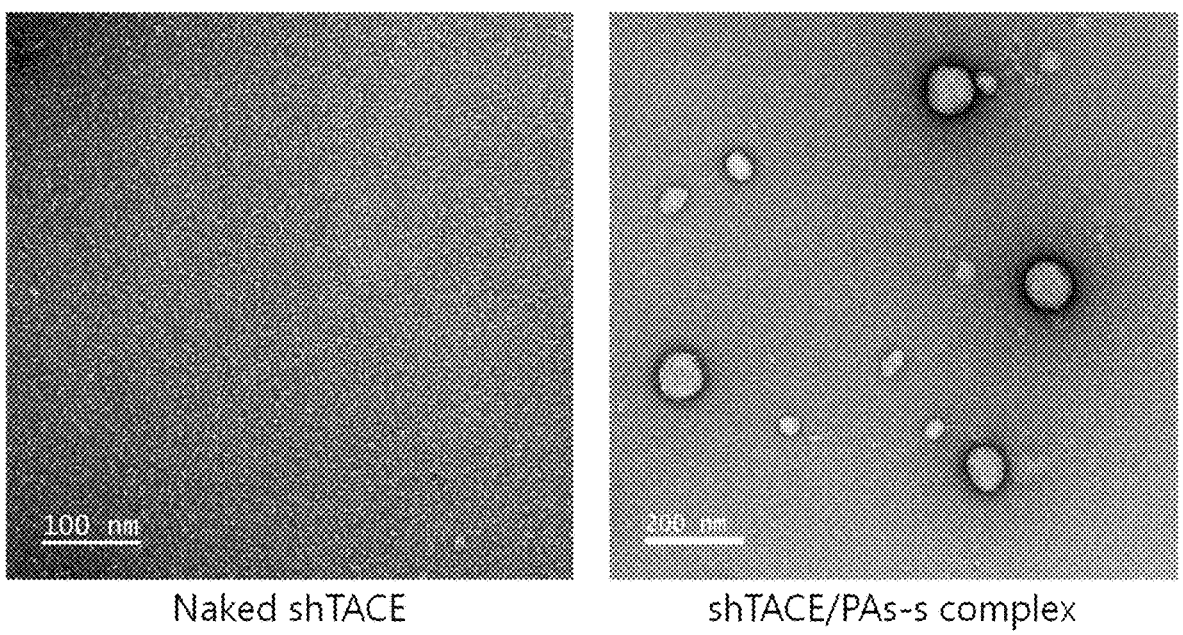

[FIG. 8]
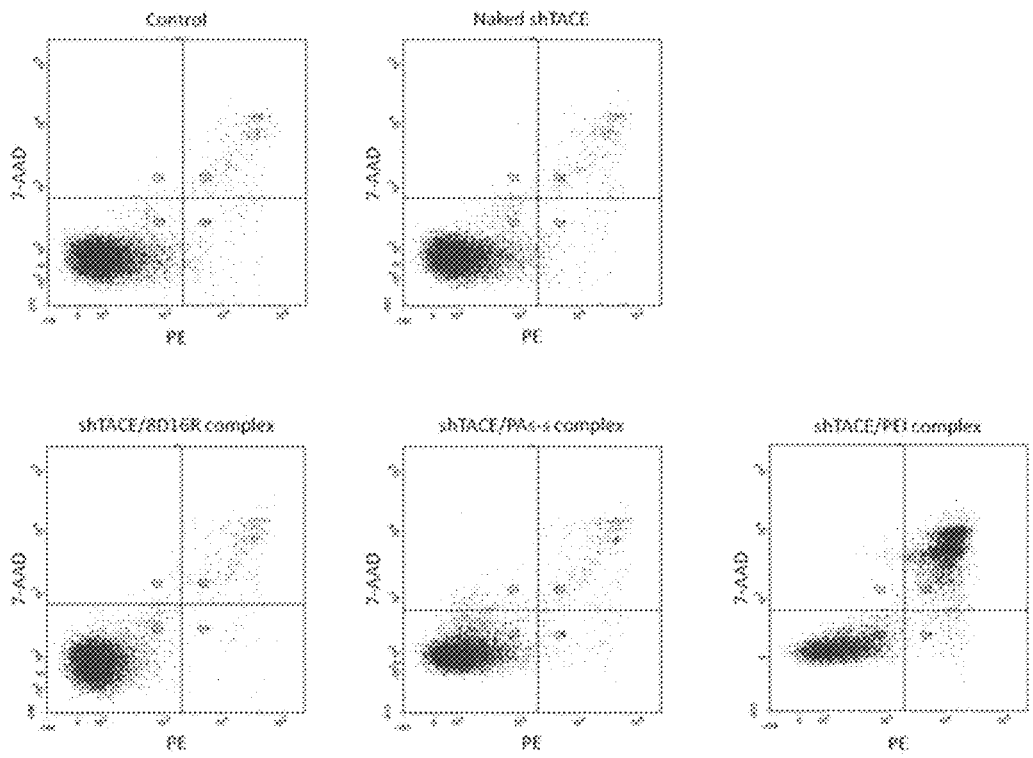
[FIG. 9]
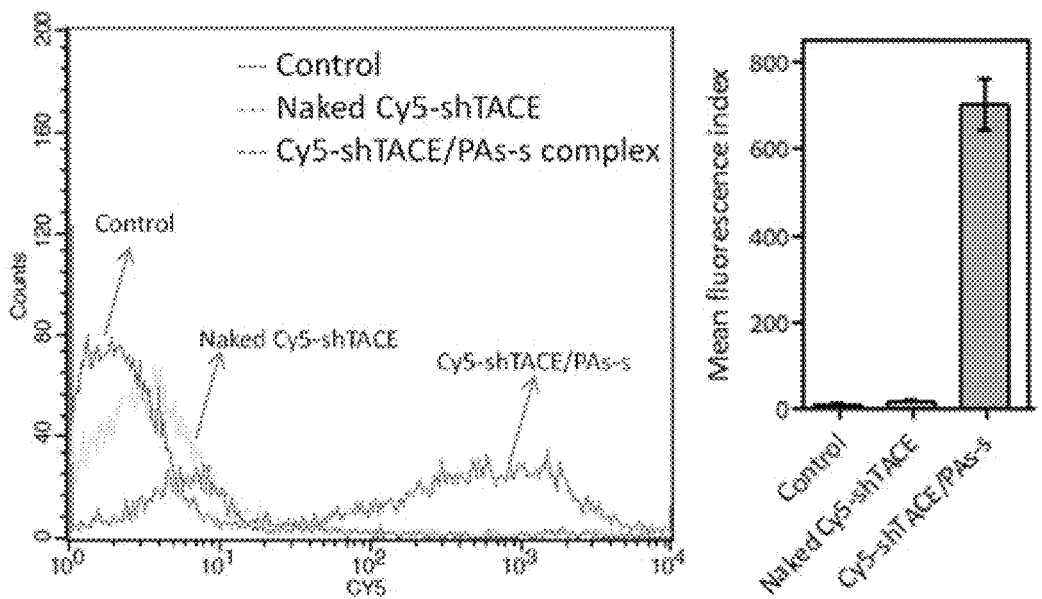

[FIG. 10]
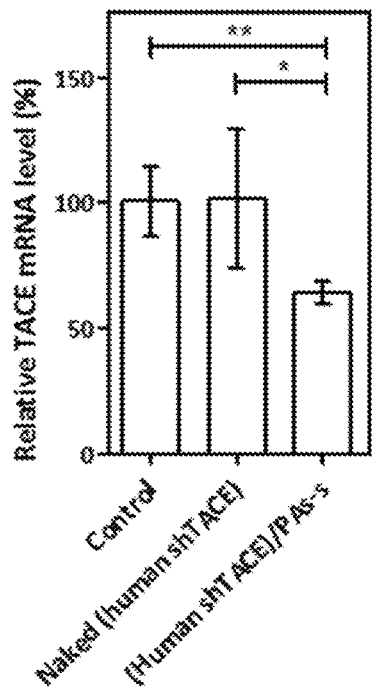
[FIG. 11]
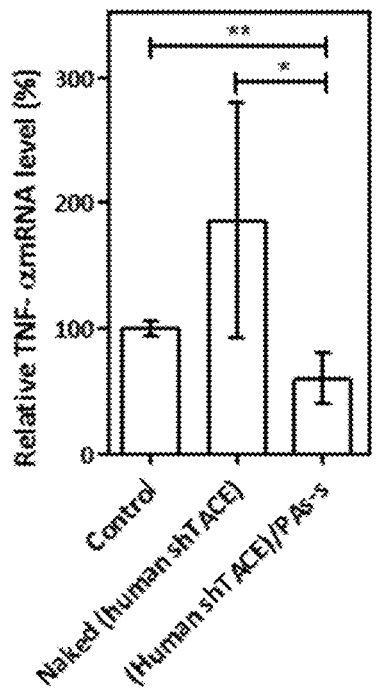

[FIG. 12]
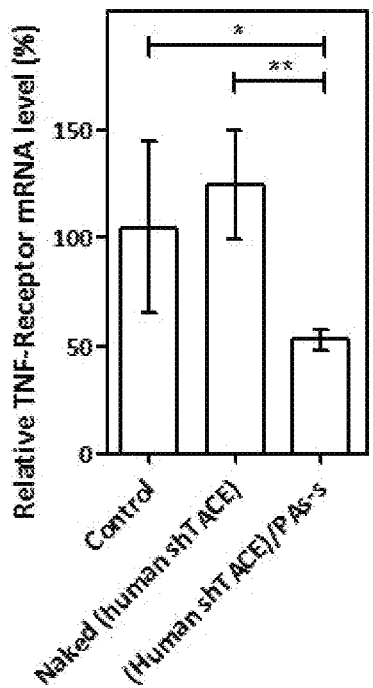
[FIG. 13]
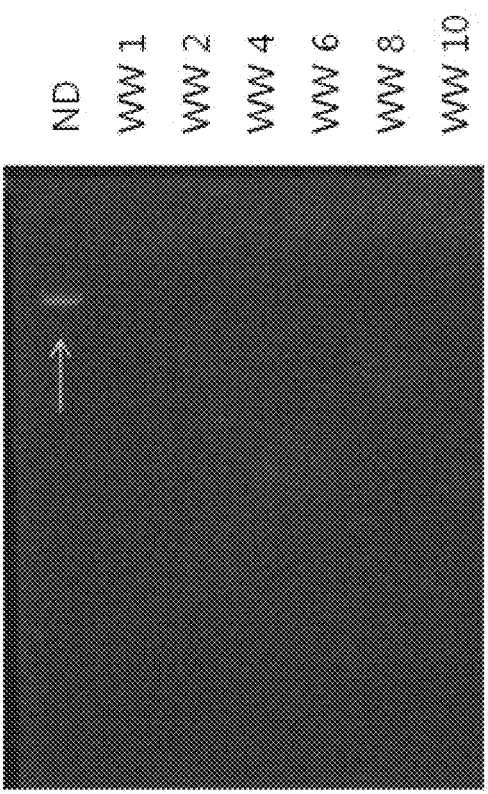

[FIG. 14]
|  | Zeta potential (mV) | Size (nm) | PDI |
|---|---|---|---|
| Average | 30.23 | 182.5 | 0.257 |
| Standard deivation | 10.77 | 16.35 | 0.026 |
[FIG. 15]
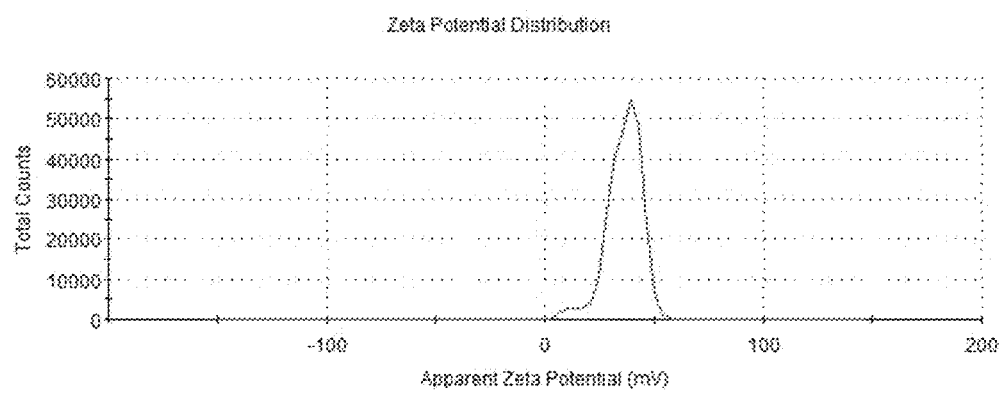
[FIG. 16]
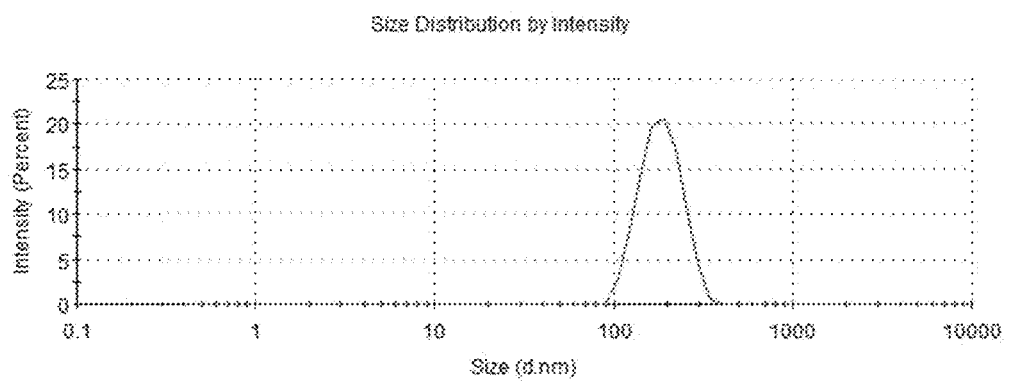

[FIG. 17]
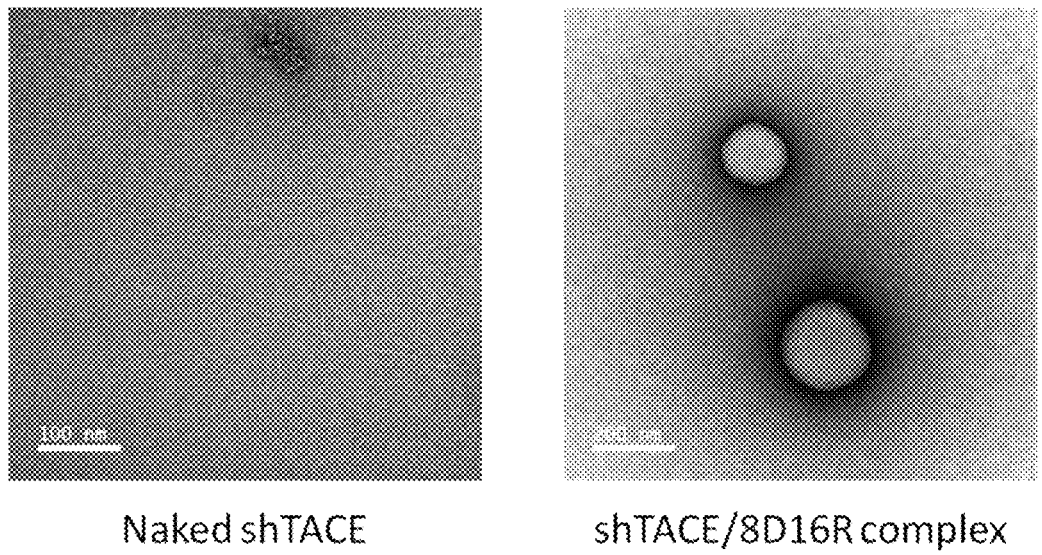
Naked shTACE         shTACE/8D16R complex
[FIG. 18]
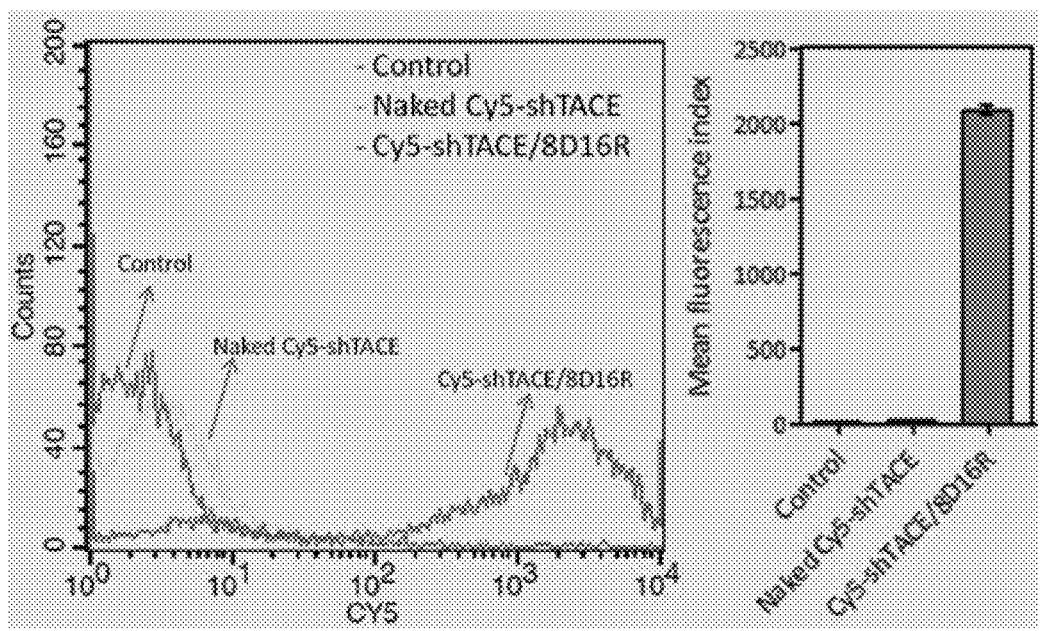

[FIG. 19]
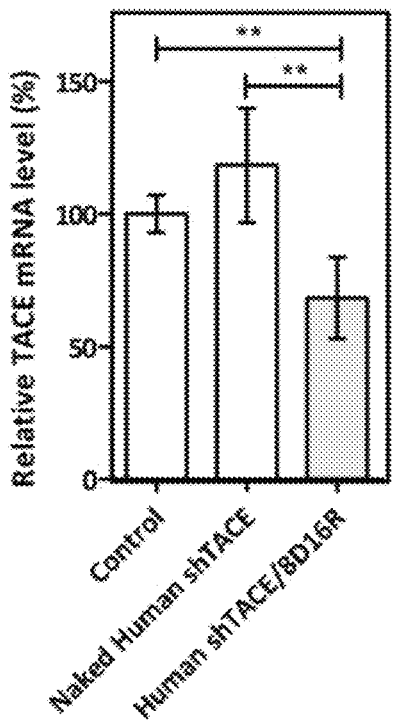
[FIG. 20]
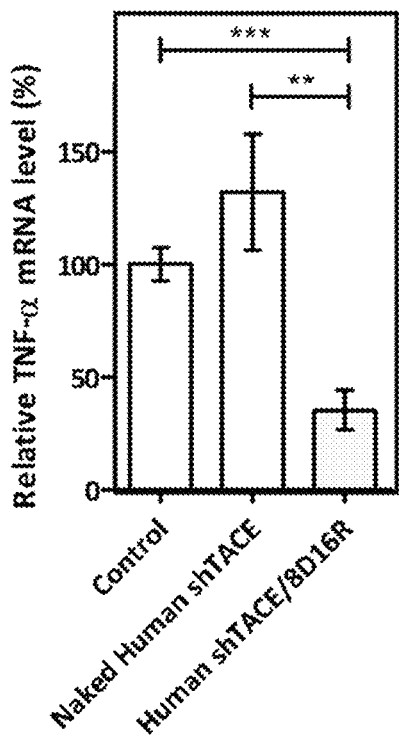

[FIG. 21]
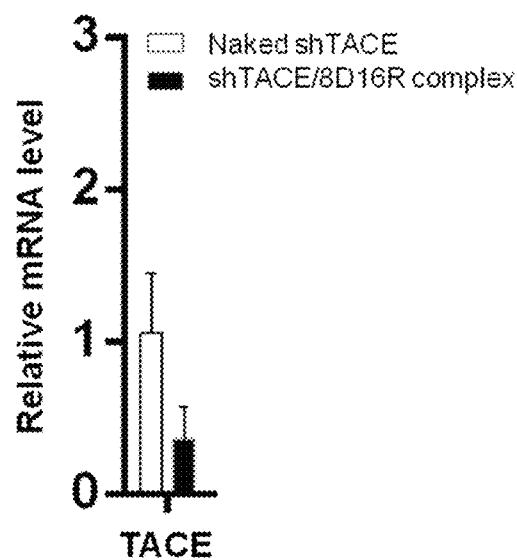
[FIG. 22]
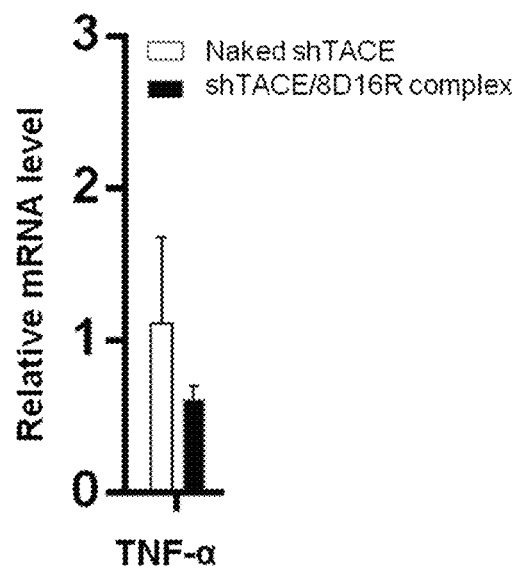

[FIG. 23]
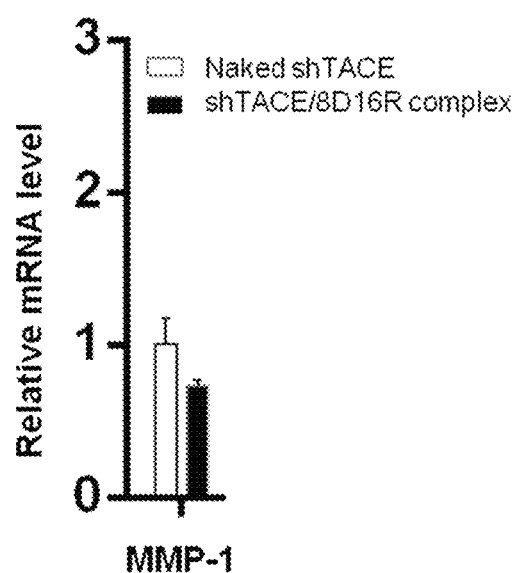
[FIG. 24]
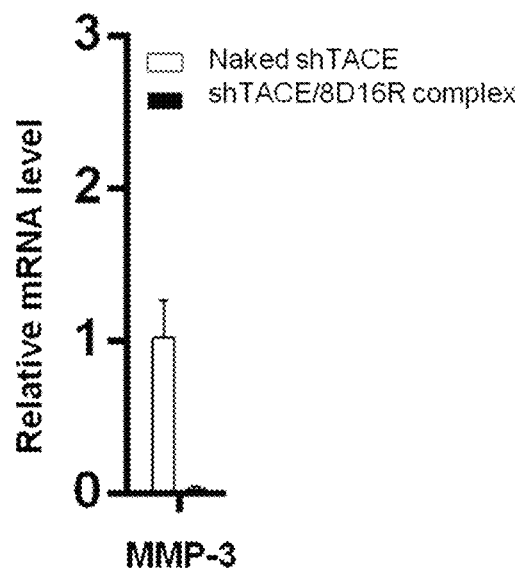

[FIG. 25]
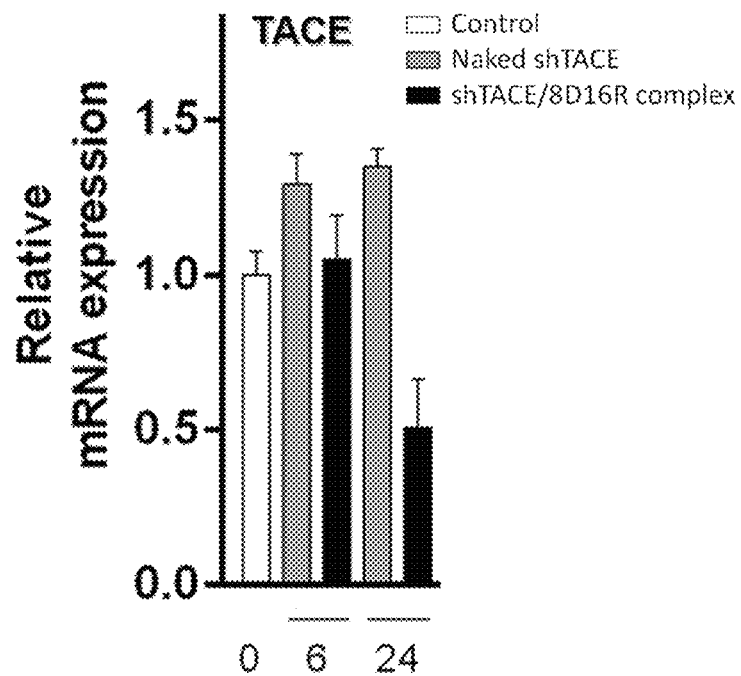
[FIG. 26]
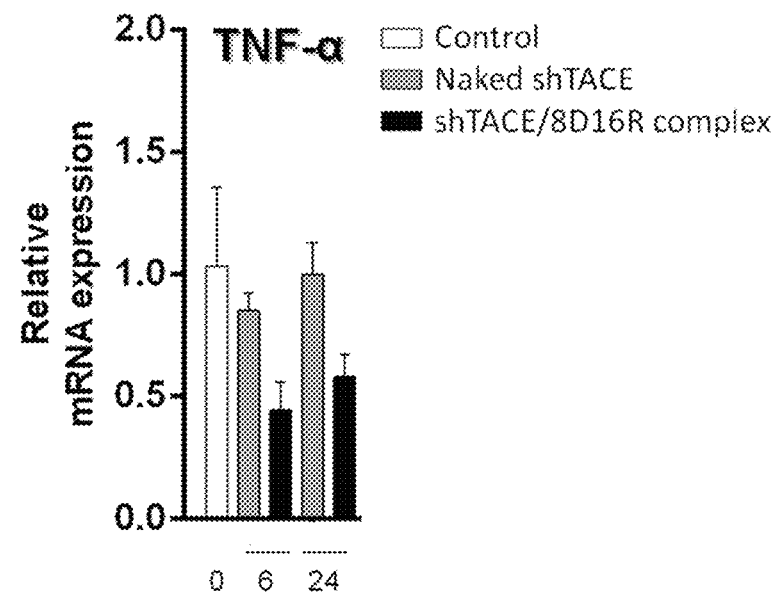

[FIG. 27]
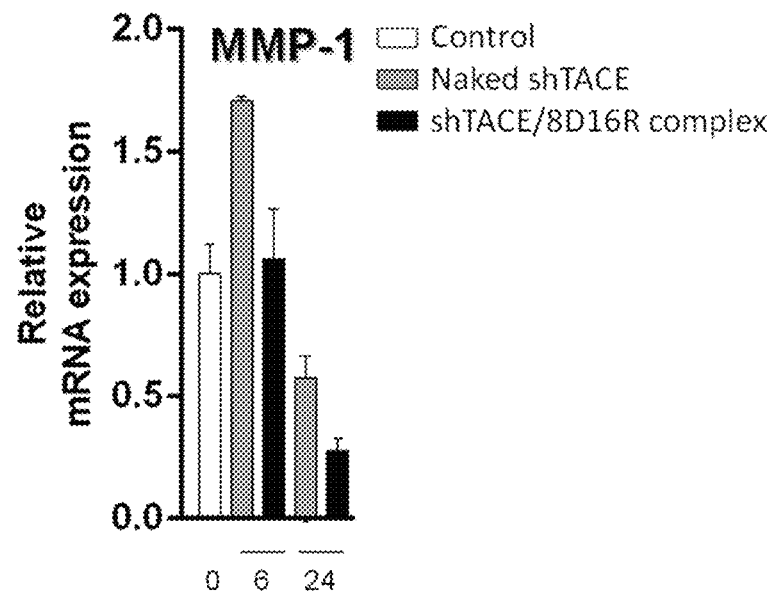
[FIG. 28]
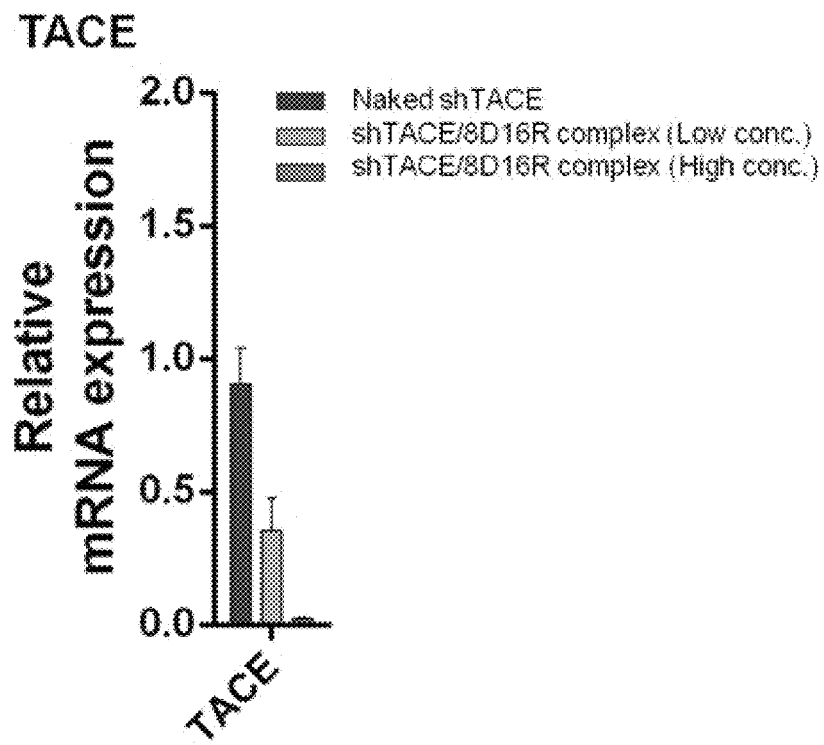

[FIG. 29]
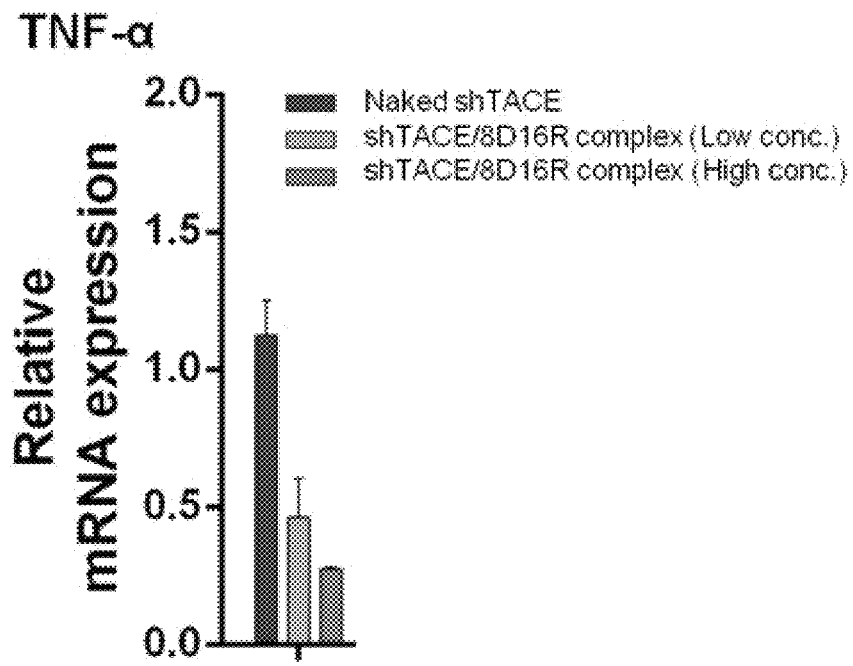
[FIG. 30]
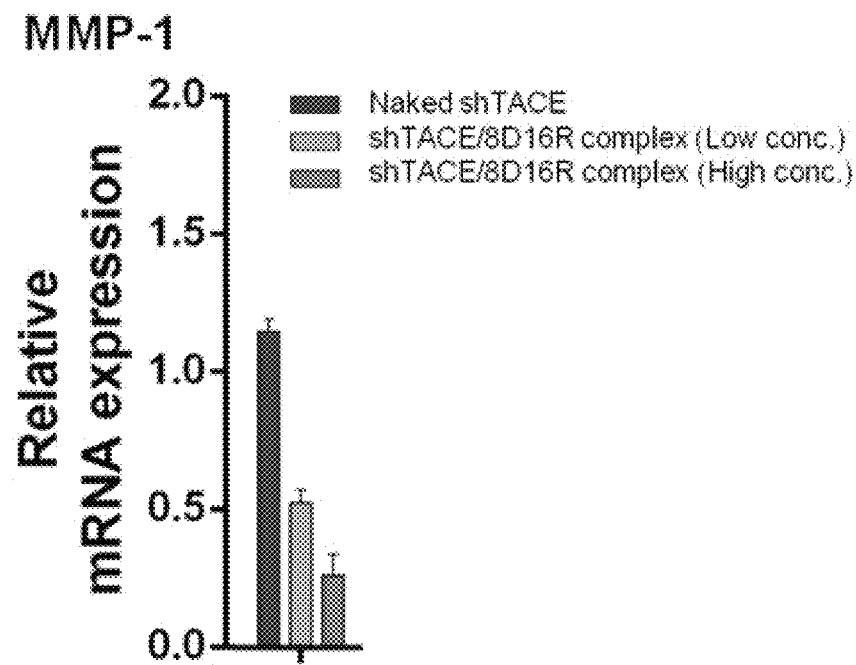

[FIG. 31]
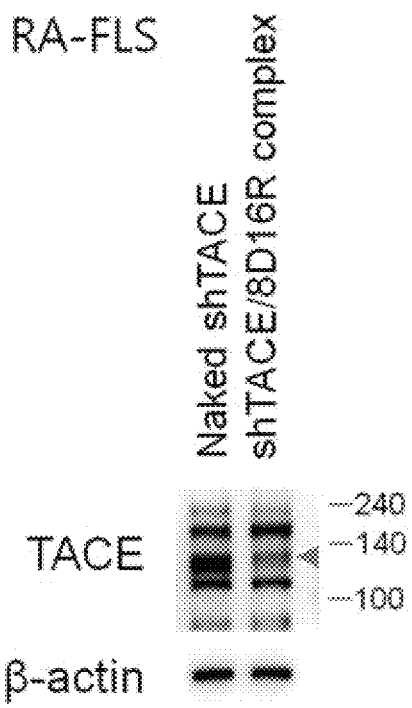
[FIG. 32]

[FIG. 33]
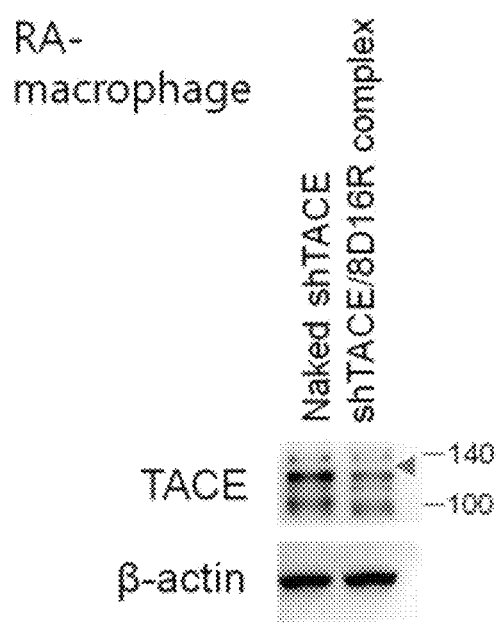

GENE/CARRIER COMPLEX FOR PREVENTING OR TREATING INFLAMMATORY DISEASES

CROSS-REFERENCE TO RELATED APPLICATION

This application is a continuation-in-part of U.S. patent application Ser. No. 15/721,199, filed Sep. 29, 2017, which in turn claims priority to the benefit of Korean Patent Application No. 2016-0126284, filed Sep. 30, 2016, Application No. 2017-0123413, filed on Sep. 25, 2017, Application No. 2017-0123414, filed on Sep. 25, 2017, the disclosure of which is incorporated herein by reference in its entirety.

SEQUENCE STATEMENT

Incorporated by reference herein in its entirety is the Sequence Listing entitled "G18U10C0390PUS_ST25," created Oct. 29, 2018, size of 5 kilobyte.

BACKGROUND

1. Field of the Invention

The prevent invention relates to a gene/carrier complex for preventing or treating inflammatory diseases.

2. Discussion of Related Art

The expression of tumor necrosis factor-α converting enzyme (TACE) is increased in various inflammatory diseases, such as rheumatoid arthritis, acute lung injury, and inflammatory bowel disease. As a result, an excessive increase in the expression of TACE leads to an increase in the level of tumor necrosis factor-α (TNF-α) and activation of the inflammatory signal system, resulting in worsening of inflammatory diseases. Therefore, it is possible to prevent and treat various inflammatory diseases by inhibiting TACE expression by introducing gene therapy agents. Use of small interfering RNA (siRNA) or short hairpin RNA (shRNA) targeting TACE is a method to lower TACE expression at the cellular level.

To obtain shRNA targeting TACE (hereinafter, referred to as "shTACE"), a therapeutic gene construct, $E.\ coli$ is transformed with the desired gene and cultured at 37° C. After culture, the transformed $E.\ coli$ is lysed to isolate the desired gene. The process of obtaining the desired gene by lysing $E.\ coli$ (i.e., Prep) is classified as Miniprep, Maxiprep, and the like according to yield and experimental procedure.

In the case of shTACE, a therapeutic gene construct, described in Non-Patent Document 1 (SOMI Kim, Master's Thesis, Graduate School of Hanyang University (February 2014), "Development of non-viral RNA interference system against TACE (Tumor necrosis factor-α converting enzyme) for the treatment of inflammatory diseases") previously reported by the present inventors, even with Maxiprep, the degree of amplification of shTACE is very low, resulting in a very low yield of shTACE. Accordingly, to amplify shTACE having an existing sequence described in Non-Patent Document 1, which is difficult to amplify using Maxiprep, it is inevitable to use Miniprep. However, the disadvantages of using Miniprep are as follows. First, gene yield obtained by Miniprep is much lower than gene yield obtained by general Maxiprep and the like. Since the yield is low when using Miniprep, Miniprep should be repeated to obtain the amount of DNA needed for experimentation. This makes the experiments cumbersome and costly. In addition, since endotoxins are not removed through the Miniprep procedure, additional experiments should be performed to remove endotoxins after obtaining genes, which inconveniences experimenters. These additional processes lower the yield and purity of the obtained gene. In particular, in the case that endotoxins are lipopolysaccharides (LPSs) found in the outer membrane of gram-negative bacteria, strong inflammatory responses may be caused in animals. Thus, endotoxins must be removed before performing animal experiments.

On the other hand, the Maxiprep procedure automatically removes endotoxins, and thus no additional procedures are required to remove endotoxins. Thus, when using Maxiprep, the yield and purity of the obtained gene may be improved. Development of a method of obtaining therapeutic gene constructs using the Maxiprep procedure is required.

In addition, since shTACE has low stability in the human body, there are limitations in applying shTACE to the human body. One goal of gene therapy is to deliver gene therapy agents into the nucleus efficiently through the cell membrane and nuclear membrane. Therefore, it is essential to study efficient gene delivery systems for gene therapy.

Accordingly, the present inventors prepared a novel gene therapy agent, in which the sequence of a shRNA that inhibits expression of a tumor necrosis factor-alpha converting enzyme (TACE) was modified, and synthesized a novel carrier capable of stably delivering the gene therapy agent. Thus, the present invention was completed by developing the gene therapy agent (gene/carrier complex) having an excellent effect on preventing or treating inflammatory diseases.

SUMMARY OF THE INVENTION

Therefore, it is an objective of the present invention to provide a gene/carrier complex including shRNA that inhibits expression of a tumor necrosis factor-alpha converting enzyme (TACE), and a nonviral gene carrier.

It is another objective of the present invention to provide a composition for preventing or treating inflammatory diseases, including the gene/carrier complex as an active ingredient.

BRIEF DESCRIPTION OF THE DRAWINGS

The above and other objects, features and advantages of the present invention will become more apparent to those of ordinary skill in the art by describing in detail exemplary embodiments thereof with reference to the attached drawings, in which:

FIG. 1 shows the results of measuring an amount of TACE mRNA in human-derived macrophages after treatment with a human shTACE/lipofectamine gene/carrier complex;

FIG. 2 shows the results of measuring an amount of TACE mRNA in osteoarthritis-derived fibroblast-like synovial cells after treatment with the human shTACE/lipofectamine gene/carrier complex;

FIG. 3 shows the results of determining, by means of electrophoresis, whether or not the human shTACE/PAs-s gene/carrier complex is formed depending on a weight ratio of the complex [ND: Naked shTACE (PAs-s carrier untreated), WW 0.5: PAs-s/shTACE=0.5, WW 1: PAs-s/shTACE=1, WW 2: PAs-s/shTACE=2, WW 4: PAs-s/shTACE=4, WW 6: PAs-s/shTACE=6, WW 8: PAs-s/shTACE=8];

FIG. 4 shows the results showing a zeta potential, a particle size and an average PDI value of the human shTACE/PAs-s gene/carrier complex when the weight ratio of the complex is 2 (PAs-s/shTACE=2);

FIG. 5 is a representative graph illustrating distribution of zeta potential values of the human shTACE/PAs-s gene/carrier complex when the weight ratio of the complex is 2 (PAs-s/shTACE=2);

FIG. 6 a representative graph illustrating distribution of particle size values of the human shTACE/PAs-s gene/carrier complex when the weight ratio of the complex is 2 (PAs-s/shTACE=2);

FIG. 7 shows the results of determining, on a transmission electron microscopy (TEM) image, the morphology of the human shTACE/PAs-s gene/carrier complex when the weight ratio of the complex is 2 (PAs-s/shTACE=2);

FIG. 8 shows the results of observing cell apoptosis in the human-derived macrophages (THP-1 cell line) after treatment with each of human shTACE/PAs-s and human shTACE/8D16R gene/carrier complexes;

FIG. 9 shows the results of measuring, by means of FACS analysis, a degree of intracellular delivery of a gene (Cy5-shTACE) with which a Cy5 fluorophore is linked via a PAs-s carrier in the human-derived macrophages (THP-1 cell line);

FIG. 10 shows the results of measuring an amount of TACE mRNA in the human-derived macrophages (THP-1 cell line) after treatment with the human shTACE/PAs-s gene/carrier complex;

FIG. 11 shows the results of measuring an amount of TNF-α mRNA in the human-derived macrophages (THP-1 cell line) after treatment with the human shTACE/PAs-s gene/carrier complex;

FIG. 12 shows the results of measuring an amount of TNF-receptor mRNA in the human-derived macrophages (THP-1 cell line) after treatment with the human shTACE/PAs-s gene/carrier complex;

FIG. 13 shows the results of determining, by means of electrophoresis, whether or not the human shTACE/8D16R gene/carrier complex is formed depending on the weight ratio of the complex [ND: Naked shTACE (8D16R carrier untreated), WW 1: 8D16R/shTACE=1, WW 2: 8D16R/shTACE=2, WW 4: 8D16R/shTACE=4, WW 6: 8D16R/shTACE=6, WW 8: 8D16R/shTACE=8, WW 10: 8D16R/shTACE=10];

FIG. 14 shows the results showing a zeta potential, a particle size and an average PDI value of the human shTACE/8D16R gene/carrier complex when the weight ratio of the complex is 4 (8D16R/shTACE=4);

FIG. 15 is a representative graph illustrating distribution of zeta potential values of the human shTACE/8D16R gene/carrier complex when the weight ratio of the complex is 4 (8D16R/shTACE=4);

FIG. 16 is a representative graph illustrating distribution of particle size values of the human shTACE/8D16R gene/carrier complex when the weight ratio of the complex is 4 (8D16R/shTACE=4);

FIG. 17 shows the results of determining, on a transmission electron microscopy (TEM) image, the morphology of the human shTACE/8D16R gene/carrier complex when the weight ratio of the complex is 4;

FIG. 18 shows the results of measuring, by means of FACS analysis, a degree of intracellular delivery of a gene (Cy5-shTACE) with which a Cy5 fluorophore is linked via an 8D16R carrier in the human-derived macrophages (THP-1 cell line);

FIG. 19 shows the results of measuring an amount of TACE mRNA in the human-derived macrophages (THP-1 cell line) after treatment with the human shTACE/8D16R gene/carrier complex;

FIG. 20 shows the results of measuring an amount of TNF-α mRNA in the human-derived macrophages (THP-1 cell line) after treatment with the human shTACE/8D16R gene/carrier complex;

FIG. 21 shows the results of measuring an amount of TACE mRNA in rheumatoid arthritis patient-derived fibroblast-like synovial cells after treatment with the human shTACE/8D16R gene/carrier complex;

FIG. 22 shows the results of measuring an amount of TNF-α mRNA in the rheumatoid arthritis patient-derived fibroblast-like synovial cells after treatment with the human shTACE/8D16R gene/carrier complex;

FIG. 23 shows the results of measuring an amount of MMP-1 mRNA in the rheumatoid arthritis patient-derived fibroblast-like synovial cells after treatment with the human shTACE/8D16R gene/carrier complex;

FIG. 24 shows the results of measuring an amount of MMP-3 mRNA in the rheumatoid arthritis patient-derived fibroblast-like synovial cells after treatment with the human shTACE/8D16R gene/carrier complex;

FIG. 25 shows the results of measuring an amount of TACE mRNA in rheumatoid arthritis patient-derived cartilage cells after treatment with the human shTACE/8D16R gene/carrier complex;

FIG. 26 shows the results of measuring an amount of TNF-α mRNA in the rheumatoid arthritis patient-derived cartilage cells after treatment with the human shTACE/8D16R gene/carrier complex;

FIG. 27 shows the results of measuring an amount of MMP-1 mRNA in the rheumatoid arthritis patient-derived cartilage cells after treatment with the human shTACE/8D16R gene/carrier complex;

FIG. 28 shows the results of measuring an amount of TACE mRNA in synovial fluid-derived CD14 positive macrophage cells of rheumatoid arthritis patients after treatment with the human shTACE/8D16R gene/carrier complex;

FIG. 29 shows the results of measuring an amount of TNF-α mRNA in the synovial fluid-derived CD14 positive macrophage cells of rheumatoid arthritis patients after treatment with the human shTACE/8D16R gene/carrier complex;

FIG. 30 shows the results of measuring an amount of MMP-1 mRNA in the synovial fluid-derived CD14 positive macrophage cells of rheumatoid arthritis patients after treatment with the human shTACE/8D16R gene/carrier complex;

FIG. 31 shows the results of measuring an expression level of a TACE protein in the rheumatoid arthritis patient-derived fibroblast-like synovial cells after treatment with the human shTACE/8D16R gene/carrier complex;

FIG. 32 shows the results of measuring an expression level of the TACE protein in the rheumatoid arthritis patient-derived cartilage cells after treatment with the human shTACE/8D16R gene/carrier complex; and FIG. 33 shows the results of measuring an expression level of the TACE protein in the synovial fluid-derived CD14 positive macrophage cells of rheumatoid arthritis patients after treatment with the human shTACE/8D16R gene/carrier complex.

DETAILED DESCRIPTION OF EXEMPLARY EMBODIMENTS

Hereinafter, the present invention will be described with reference to examples and comparative examples in detail. However, the present invention is not limited to these examples.

The present invention relates to a gene/carrier complex including shRNA that inhibits expression of a tumor necrosis factor-alpha converting enzyme (TACE), and a nonviral gene carrier.

Hereinafter, the present invention is described in detail as follows.

The present inventors developed a novel shTACE, in which the sequence of a conventional shTACE was modified, to solve the problems of the conventional shTACE. The novel shTACE construct may be applied to both Miniprep and Maxiprep. The novel gene construct has excellent amplification rate when using Miniprep and Maxiprep, and thus may be obtained in a high yield. Therefore, the novel shTACE has a cost advantage compared with the conventional gene construct, which is limited to use of Maxiprep and requires repeated Prep (e.g., Miniprep) due to low yield. In addition, since endotoxins are automatically removed during a Maxiprep experiment, the prepared shTACE may be injected into the body immediately after obtaining the shTACE.

A novel human shTACE of the present invention has a base sequence set forth in one or more selected from the group consisting of SEQ ID NOS: 2 to 5. The shRNA may be in the form such that it is contained in a plasmid vector, and the plasmid vector containing the shRNA has one or more base sequences selected from the group consisting of SEQ ID NOS: 7 to 10.

Since a gene has a negative charge due to phosphates thereof, it cannot easily penetrate the cell membrane exhibiting a negative charge due to electrical repulsion between the gene and the cell membrane. Therefore, when a gene reacts with a substance exhibiting a positive charge to form a complex in which a net charge is positive, the complex including the gene may enter the cell more easily, and as a result, the gene may be expressed within the cell. Such a substance that enhances gene delivery into cells is called a gene carrier. The gene carrier refers to a substance that binds to a gene and promotes gene delivery to enhance intracellular expression of the gene. Such gene carriers are mostly positively charged, and a gene/carrier complex is formed by electrical interaction between a negatively charged gene and a positively charged gene carrier.

According to one embodiment of the present invention, the low stability of shTACE may be overcome by using a nonviral gene carrier (hereinafter, referred to as "PAs-s") including the acetate of disulfide-linked poly(oligo-arginine).

The disulfide-linked poly(oligo-arginine) may be composed of nine-arginine oligomers, wherein each nine-arginine oligomer includes disulfide-linked cysteines at both ends thereof.

The disulfide-linked poly(oligo-arginine) may include a repeating unit of Cys-(9×Arg)-Cys, and the thiol groups of cysteines at both ends of the repeating unit may be polymerized via disulfide crosslinking.

First, a monomeric peptide of Cys-(9×Arg)-Cys may be synthesized using Fmoc solid-phase peptide synthesis, in which each amino acid is extended one by one according to a predetermined sequence order and the α-amino group of the amino acid is protected with a 9-fluorenyl-methyloxy-carbonyl (Fmoc) group. When a step of elongating the peptide chain is completed, a released form of the peptide is obtained by treatment with trifluoroacetic acid (TFA). Subsequently, a monomeric peptide of Cys-(9×Arg)-Cys in a TFA salt form is converted into an acetate form. That is, the TFA salt is substituted with acetate using ion exchange chromatography with AG1-X8 resins.

The monomeric peptide of Cys-(9×Arg)-Cys in an acetate form is subjected to an oxidative polymerization reaction, in which disulfide bonds between cysteines are formed, and as a result, a polymeric gene carrier is formed.

In the case of PAs-s used as a gene carrier in the present invention, the basic salt form of the gene carrier is changed from a TFA salt to an acetate form, unlike conventional gene carriers. This may minimize side effects that may occur when the gene carrier is injected into the body, and may further improve the ability of the gene carrier to carry a gene in the body compared to conventional gene carriers.

The human shTACE and PAs-s form a complex via electrical interaction. To form a gene/carrier complex (peptoplex) with an excellent therapeutic effect, the ratio of a gene to a gene carrier should be optimally adjusted when the complex is formed. There are various kinds of ratios such as weight ratio, charge ratio, and nitrogen/phosphorous (N/P) ratio. In the present invention, a weight ratio is used. In the gene/carrier complex according to the present invention, TACE shRNA and the PAs-s gene carrier are preferably mixed in a weight ratio of 1:1.5 to 8 or 1:1.5 to 4.

In addition, according to one embodiment of the present invention, the low stability of shTACE may be overcome by using a nonviral gene carrier (hereinafter, referred to as PDPR) including the trifluoroacetic acid (TFA) salt of poly (oligo-aspartic acid) (oligo-arginine).

The poly(oligo-aspartic acid)(oligo-arginine) may include cysteines at both ends thereof.

The poly(oligo-aspartic acid)(oligo-arginine) may include cysteines at both ends thereof and may be composed of an eight-aspartic acid oligomer and a sixteen-arginine oligomer.

The poly(oligo-aspartic acid)(oligo-arginine) may refer to a Cys-(8×Asp)-(16×Arg)-Cys peptide.

First, a Cys-(8×Asp)-(16×Arg)-Cys peptide may be synthesized using Fmoc solid-phase peptide synthesis, in which each amino acid is extended one by one according to a predetermined sequence order and the α-amino group of the amino acid is protected with a 9-fluorenyl-methyloxycarbonyl (Fmoc) group. When a step of elongating the peptide chain is completed, a released form of the peptide is obtained by treatment with trifluoroacetic acid (TFA).

According to one embodiment of the present invention, a TFA salt of 'Cys-(8Asp)-(16Arg)-Cys' (hereinafter referred to as '8D16R') is used as the nonviral gene carrier.

Unlike conventional gene carriers, the PDPR gene carrier used in the present invention is characterized in that the PDPR gene carrier is composed of a peptide targeting a bone resorption site and a peptide capable of increasing the intracellular delivery efficiency of the peptide. This may minimize side effects that may occur when the gene carrier is injected into the body, and may further improve the ability of the gene carrier to carry a gene in the body compared to conventional gene carriers.

The human shTACE and PDPR form a complex via electrical interaction. To form a gene/carrier complex (peptoplex) with an excellent therapeutic effect, the ratio of a gene to a gene carrier should be optimally adjusted when the complex is formed. There are various kinds of ratios such as weight ratio, charge ratio, and nitrogen/phosphorous (N/P) ratio. In the present invention, weight ratio is used. In the gene/carrier complex according to the present invention, TACE shRNA and the PDPR gene carrier (ex., 8D16R) are preferably mixed in a weight ratio of 1:1.5 to 8 or 1:2 to 6.

In addition, the present invention provides a method of preparing a gene/carrier complex, the method including a step of mixing and incubating shRNA that inhibits expression of a tumor necrosis factor-alpha converting enzyme (TACE), and a nonviral carrier.

To obtain an optimal gene/carrier complex, incubation is preferably performed at 20 to 40° C. for 20 to 40 minutes. At higher temperatures above 40° C., hydrogen bonds between strands of DNA break, resulting in DNA denaturation. Since a carrier is produced by polymerization of peptides and is therefore denatured at high temperature, the incubation is preferably performed at a temperature of 40° C. or below. Furthermore, cells are preferably treated with the complex at a temperature similar to a body temperature. In addition, when the incubation is performed for more than 40 minutes, the gene and the gene carrier form a precipitate, so that it is preferable that the incubation time not exceed 40 minutes. Also, after the gene and the carrier form a complex via electrical attraction, it is preferable to incubate the complex for at least 20 minutes to maintain the state of the complex stably.

The shTACE exhibits a negative charge, and PAs-s or PDPR exhibits a positive charge. When the two components are mixed and incubated at room temperature for about 20 to 40 minutes, a gene/carrier complex may be formed via electrostatic attraction. After complex formation, the final volume is adjusted using deionized/distilled water, PBS, and the like for each group.

To determine the optimal weight ratio of a gene/carrier complex, the concentrations of a gene and a gene carrier should first be determined, respectively. Since the amount of ultraviolet radiation absorbed is proportional to the amount of DNA, the concentration of the gene is measured using an ultraviolet spectrophotometer. It is preferable to prepare the gene at a concentration of 1 mg/ml or less to prevent precipitation of the gene/carrier complex. The gene carrier may be synthesized at a final concentration of 1 mg/ml by adjusting the amount of HEPES buffer.

Any of the above-described contents relating to the gene/carrier complex may be directly applied to the method of preparing the gene/carrier complex.

In addition, the present invention provides a pharmaceutical composition for preventing or treating inflammatory diseases, including the gene/carrier complex as an active ingredient.

Also, the present invention provides a method of preventing or treating inflammatory diseases, which includes administering the pharmaceutical composition to a subject.

As used herein, the term "subject" may refer to a vertebrate to be treated, observed or tested, preferably a mammal such as, for example, a cow, a pig, a horse, a goat, a dog, a cat, rat, a mouse, a rabbit, a guinea pig, a human, and the like.

As used herein, inflammatory diseases may include one or more selected from the group consisting of ocular inflammation, allergic conjunctivitis, dermatitis, rhinitis, asthma, rheumatoid arthritis, acute lung injury, inflammatory bowel disease, and obesity.

As used herein, the term "ocular inflammation" may include, for example, iritis, uveitis, episcleritis, scleritis, keratitis, endophthalmitis, blepharitis, and iatrogenic inflammatory conditions.

As used herein, the term "allergic conjunctivitis" refers to inflammation of the conjunctiva located in the eyelid and covering the exposed surface of the sclera. "Allergic conjunctivitis" may include, for example, atopic keratoconjunctivitis, giant papillary conjunctivitis, hay fever conjunctivitis, perennial allergic conjunctivitis, and vernal keratoconjunctivitis.

As used herein, the term "dermatitis" refers to inflammation of the skin and may include, for example, allergic contact dermatitis, hives, non-sebaceous dermatitis (dry skin of legs), atopic dermatitis, contact dermatitis (e.g., irritant contact dermatitis and lacquer-induced contact dermatitis), eczema, gravitational dermatitis, nummular dermatitis, otitis externa, perioral dermatitis, and seborrheic dermatitis.

As used herein, the term "rhinitis" refers to inflammation of the nasal mucosa and may include, for example, allergic rhinitis, atopic rhinitis, irritant rhinitis, acidophilic non-allergic rhinitis, medicamentous rhinitis, and neutrophilic rhinosinusitis.

As used herein, the term "asthma" refers to inflammation of the respiratory tract causing stenosis of the airways moving air from the nose and mouth to the lungs and may include, for example, allergic asthma, atopic asthma, atopic bronchus IgE-mediated asthma, bronchus asthma, bronchiolitis, emphysematous asthma, essential asthma, exercise-induced asthma, exogenous asthma induced by environmental factors, incipient asthma, endogenous asthma caused by pathophysiological disorders, non-allergic asthma, non-atopic asthma, and wheezy infant syndrome.

As used herein, the term "rheumatoid arthritis" is an inflammatory systemic autoimmune disease. When the disease occurs, the synovial membrane is mainly attacked by the autoimmune system. The cause of the disease is unknown, and the symptoms thereof include polyarthritis and chronic inflammation in various tissues and organs. Thus, rheumatoid arthritis is also a type of chronic inflammatory disease.

As used herein, the term "acute lung injury" refers to damage due to acute inflammation of the lungs, where the epithelial and endothelial cells of the lungs are damaged. Symptoms include respiratory failure and arterial hypoxemia.

As used herein, the term "obesity" refers to a state of excessive fat tissue in the body. Obesity is a low-stage inflammatory disease and may cause metabolic syndrome such as type 2 diabetes.

As used herein, the term "inflammatory bowel disease" refers to severe chronic inflammation caused by inflammatory agents (e.g., inflammatory cytokines) in the gastrointestinal tract, and specific examples thereof may include Crohn's disease, ulcerative colitis, intestinal Behcet's disease, simple ulcers, radiation enteritis, and ischemic colitis.

The pharmaceutical composition of the present invention may be administered together with a pharmaceutically acceptable carrier. Upon oral administration, the pharmaceutical composition may further contain, in addition to an active ingredient, a binder, a lubricant, a disintegrant, an excipient, a solubilizer, a dispersant, a stabilizer, a suspending agent, a pigment, a perfume, and the like. When the pharmaceutical composition of the present invention is injected, the pharmaceutical composition may be mixed with a buffer, a preservative, a pain relief agent, a solubilizer, an isotonic agent, a stabilizer, and the like. Upon topical administration, the composition of the present invention may include a base, an excipient, a lubricant, a preservative, and the like.

Formulations of the composition of the present invention may be prepared in a variety of ways by mixing with pharmaceutically acceptable carriers as described above. For example, upon oral administration, the composition of the present invention may be prepared in the form of tablets, troches, capsules, elixirs, suspensions, syrups, wafers, and the like. When the composition of the present invention is injected, the composition may be prepared in unit dose ampoules or in multiple unit dose forms. The composition of the present invention may be formulated into other solutions, suspensions, tablets, pills, capsules, sustained release formulations, and the like.

In addition, examples of suitable carriers, excipients, and diluents for formulation may include lactose, dextrose, sucrose, sorbitol, mannitol, xylitol, erythritol, maltitol, starch, acacia, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, mineral oil, and the like. In addition, fillers, anti-coagulants, lubricants, wetting agents, perfumes, preservatives, and the like may be further included in the formulation The pharmaceutical composition of the present invention may be administered orally or parenterally. For examples, the pharmaceutical composition may be administered through oral, aerosol, buccal, epidermal, intradermal, inhalation, intramuscular, intranasal, intraocular, intrapulmonary, intravenous, intraperitoneal, nasal, ocular, oral, ear, injection, patch, subcutaneous, hypoglossal, topical or percutaneous routes, without being limited thereto.

For clinical administration, the pharmaceutical composition of the present invention may be formulated into a suitable formulation using known techniques. For example, upon oral administration, the composition may be mixed with an inert diluent or edible carrier, sealed in a hard or soft gelatin capsule, or tableted. For oral administration, the active ingredient of the composition may be mixed with an excipient and used in the form of ingestible tablets, buccal tablets, troches, capsules, elixirs, suspensions, syrups, wafers, and the like. In addition, various formulations for injection, parenteral administration, and the like may be prepared according to known techniques or conventional techniques in the art.

The effective dose of the pharmaceutical composition of the present invention may be determined depending on the patient's body weight, age, sex, health conditions, diet, administration time, administration method, excretion rate, disease severity, and the like, and may be easily determined by an ordinary export in the art.

The preferred dosage of the pharmaceutical composition of the present invention may vary depending on the condition and weight of the patient, the degree of disease, the type of drug, the route of administration, and the duration of administration, and may be appropriately selected by those skilled in the art. Preferably, the composition is administered at a daily dose of 0.001 to 100 mg/kg body weight, more preferably 0.01 to 30 mg/kg body weight. Administration may be carried out once or several times a day. The gene carrier complex of the present invention may be present in an amount of 0.0001 to 10% by weight, preferably 0.001 to 1% by weight, with respect to 100% by weight of the total composition.

The pharmaceutical composition of the present invention may be administered to mammals such as rats, mice, livestock, and humans via various routes. There are no limitations on the method of administration, and for example, the composition may be administered orally or rectally, or by intravenous, intramuscular, subcutaneous, intrauterine dural or intracerebroventricular injection.

Hereinafter, the present invention will be described in detail with reference to examples. However, the following examples are illustrative of the present invention, and the present invention is not limited to the following examples.

EXAMPLES

Preparation Example 1: Preparation of Mouse shTACE Vector

A plasmid vector including mouse shRNA (shTACE), which inhibits TACE expression with a RNA interference system, consists of a total of 6,669 base pairs, and has a U6 promoter. A vector was constructed by inserting mouse shTACE having a sequence of 19 bases (ACACCTGCTG-CAATAGTGA) thereinto to selectively inhibit only TACE expression. For propagation and expression of the vector, an SV40 origin and a pUC origin were used. An ampicillin-resistant gene was added, and cells were transfected with the ampicillin-resistant gene. Thereafter, puromycin was used as a selection marker to separate the cells in which shTACE was stably expressed. To determine whether or not the mouse shTACE gene was properly inserted into the vector, a vector was constructed using an eGFP reporter gene. A sequence of a hairpin loop in the vector was TCAAGAG. A sequence of the mouse shTACE vector thus constructed was set forth in SEQ ID NO: 6.

Meanwhile, a therapeutic effect of the gene therapy system of the present invention was verified through animal experiments using mice.

Preparation Example 2: Preparation of Human shTACE Vector

A plasmid vector including human shRNA (shTACE), which inhibits TACE expression, consists of a total of 6,673 base pairs, and has a U6 promoter. A vector was constructed by inserting human shTACE having a sequence of 21 bases thereinto to selectively inhibit only TACE expression. A total of 4 types of human shTACE were obtained depending on the type of the inserted 21-base sequence (human shTACE). Specifically, they were named human shTACE #1 (SEQ ID NO: 2) having a base sequence of ggagatttgttaatgatacca, human shTACE #2 (SEQ ID NO: 3) having a base sequence of cctggttacaactcatgaatt, human shTACE #3 (SEQ ID NO: 4) having a base sequence of ggcgattaatgctacttgcaa, and human shTACE #4 (SEQ ID NO: 5) having a base sequence of ccattgtgtggataagaaatt. For propagation and expression of the vector, an SV40 origin and a pUC origin were used. An ampicillin-resistant gene was added, and cells were transfected with the ampicillin-resistant gene. Thereafter, puromycin was used as the selection marker to separate the cells in which human shTACE was stably expressed. To determine whether or not the human shTACE gene was properly inserted into the vector, a vector was constructed using an eGFP reporter gene. A sequence of a hairpin loop in the vector was TCAAGAG. Sequences of the human shTACE vectors thus constructed were set forth in SEQ ID NO: 7 (containing shTACE sequence #1), SEQ ID NO: 8 (containing shTACE sequence #2), SEQ ID NO: 9 (containing shTACE sequence #3), and SEQ ID NO: 10 (containing shTACE sequence #4).

For clinical application of this system, experiments had to be performed on advance in human cell lines. Non-toxic, anti-inflammatory effects of this gene therapy agent should be verified in human-derived cells. In this case, a human shTACE gene should be used instead of the mouse shTACE gene. Among the various sequences of the human shTACE vectors, a combination of the following gene carrier and a vector sequence, which maximally inhibits TACE expression, may be used as the optimal gene/carrier complex.

Preparation Example 3: Preparation of Gene Carrier (PAs-s)

A gene carrier (PAs-s) including the acetate of disulfide-linked poly(oligo-arginine) is formed by polymerizing a monomeric peptide of Cys-(9×Arg)-Cys represented by SEQ ID NO: 11, in which a nine-arginine oligomer including cysteines at both ends thereof is a basic repeating unit.

First, a monomeric peptide of Cys-(9×Arg)-Cys was synthesized using Fmoc solid-phase peptide synthesis, in which each amino acid was extended one by one according to a predetermined sequence order and the α-amino group of the amino acid was protected with a 9-fluorenyl-methyloxycarbonyl (Fmoc) group. When a step of elongating the peptide chain was completed, a released form of the peptide was obtained by treatment with trifluoroacetic acid (TFA). Subsequently, a monomeric peptide of Cys-(9×Arg)-Cys in a TFA salt form was converted into an acetate form. That is, the TFA salt was substituted with acetate using ion exchange chromatography with AG1-X8 resins.

A monomeric peptide of Cys-(9×Arg)-Cys in an acetate form was subjected to oxidative polycondensation, in which disulfide bonds between cysteines were formed, and as a result, the acetate of disulfide-linked poly(oligo-arginine), a polymeric carrier, was formed. For the oxidative polymerization reaction, the peptide of Cys-(9×Arg)-Cys was added to PBS containing 30% dimethyl sulfoxide (DMSO) and stirred for 6 days at a rate of 150 rpm. After stirring, the reaction was terminated by adding a HEPES buffer at a concentration of 5 mmol/L.

Preparation Example 4: Preparation of Gene Carrier (8D16R)

Preparation of a gene carrier (8D16R) was commissioned by Peptron Company (Daejeon, Korea). The gene carrier including the TFA salt of poly(oligo-aspartic acid)(oligo-arginine) includes a peptide of Cys-(8×Asp)-(16×Arg)-Cys represented by SEQ ID NO: 12, which is composed of eight aspartic acids and sixteen arginines and has cysteines at both ends thereof.

First, a peptide of Cys-(8×Asp)-(16×Arg)-Cys was synthesized using Fmoc solid-phase peptide synthesis, in which each amino acid was extended one by one according to a predetermined sequence order and the α-amino group of the amino acid was protected with a 9-fluorenyl-methyloxycarbonyl (Fmoc) group. When a step of elongating the peptide chain was completed, a released form of the peptide (8D16R) was obtained by treatment with trifluoroacetic acid (TFA).

When a step of elongating the peptide chain was completed, the Cys-(8×Asp)-(16×Arg)-Cys peptide was weighed, and the concentration thereof was adjusted with deionized/distilled water.

Experimental Example 1: Preparation of shTACE/gene carrier complex and evaluation of effectiveness thereof.

Experimental Procedure

<Agarose Gel Electrophoresis>

1 μg of human shTACE was mixed with varying amounts (1, 2, 4, 6, 8, 10 μg) of the carrier 8D16R or varying amounts (0.5, 1, 2, 4, 6, 8 μg) of the carrier PAs-s, and incubated at room temperature for 30 minutes to form a gene/carrier complex (an shTACE/8D16R peptoplex or an shTACE/PAs-s peptoplex). Thereafter, the gene/carrier complex was electrophoresed at 100 V for 20 minutes on 0.8% (wt/vol) agarose gel in a 0.5×TBE buffer to determine whether or not the complex was formed.

<Measurement of Surface Charge and Size of Complex>

5 μg of human shTACE and 20 μg of 8D16R were mixed (8D16R/shTACE=4), and incubated for 30 minutes to form a human shTACE/8D16R complex whose whole volume was then adjusted to 800 μL. Alternatively, 5 μg of human shTACE and 10 μg of PAs-s were mixed (PAs-s/shTACE=2), and incubated for 30 minutes to form a human shTACE/PAs-s complex whose whole volume was then adjusted to 800 μL. The surface charge and size of the complex were measured using a Zeta sizer-ZS (Malvern) instrument.

<Observation of Shape of Complex Using TEM>

To observe a shape of the human shTACE/carrier complex, energy-filtered transmission microscopy (EF-TEM) (EM9120, Carl Zeiss Vision GmbH, Germany) was used. First, 10 μg of human shTACE was incubated with 20 μg of a PAs-s carrier or 40 μg of an 8D16R carrier for 30 minutes to form a gene/carrier complex (an shTACE/PAs-s peptoplex or an shTACE/8D16R peptoplex). Thereafter, the sample were dried at 50° C. on a TEM grid, and then negatively stained with uranyl acetate. Then, the sample was observed and analyzed using TEM.

<Cell Culture>

Dulbecco's Modified Eagle medium (DMEM), RPMI 1640 medium, and fetal bovine serum (FBS) were purchased from WelGENE Inc. (Korea). Human-derived macrophages (THP-1 cell line), were purchased from the Korean Cell Line Bank and subcultured once every three days. Cells were cultured in complete medium supplemented with 10% FBS, penicillin (100 IU/ml), and streptomycin (100 μg/ml) at 37° C. and 5% CO2 atmospheric conditions.

<Confirmation of Non-Toxicity of Gene/Carrier Complex Using Facs>

Non-toxicity of the gene/carrier complex was determined with respect to the degree of cell apoptosis using a fluorescence-activated cell sorting (FACS) assay. Human-derived macrophages (THP-1) were seeded in 2 mL of a complete medium (CM) at a cell density of $1.5 \times 10^5$, and incubated for 24 hours in a cell culture well plate. The cells were treated with the human shTACE/PAs-s complex or the human shTACE/8D16R complex for 24 hours. Cells treated with a human shTACE/polyethyleneimine (shTACE/PEI) complex were used as the positive control. Thereafter, the cells of each group were harvested by centrifugation at 2,300 rpm for 5 minutes, and then treated with phycoerythrin (PE)-annexin V and 7-amino-actinomycin (7-AAD). When the cells reacted with annexin V, this means early-stage cell apoptosis, whereas, when the cells reacted with 7-AAD, this means late-stage cell apoptosis <Confirmation of Degree of Intracellular Delivery Using FACS>

A degree of intracellular delivery of a gene by a gene carrier was determined using a fluorescence-activated cell sorting (FACS) assay. Human-derived macrophages (THP-1) were seeded in 2 mL of a complete medium (CM) at a cell density of $1.5 \times 10^5$, and incubated for 24 hours in a cell culture well plate.

shTACE with which a Cy5 fluorophore was linked (Cy5-shTACE) was used as the gene. After the 24-hour cell culture, the shTACE with which the Cy5 fluorophore was linked (Cy5-shTACE) was mixed with a PAs-s carrier or an 8D16R carrier in the human-derived macrophages, which were then treated with the complex (an shTACE/PAs-s peptoplex or an shTACE/8D16R peptoplex). A complex including 1 μg of a gene and 2 μg of a PAs-s carrier or 1 μg of a gene and 4 μg of a 8D16R carrier were treated in a plain medium (PM) as the gene/carrier complex with which the cells were treated. After 6 hours, the cells of each group were obtained by centrifugation (at 12,470 g for 3 minutes). The cells were washed with PBS, and then analyzed for the Cy5 fluorophore using FACS.

<RNA Isolation and Real-Time PCR>

Each of a human-derived macrophage cell line (a THP-1 cell line), rheumatoid arthritis patient-derived fibroblast-like synovial cells, and rheumatoid arthritis patient-derived cartilage cells were cultured for 24 hours in a cell culture well plate. The human-derived macrophage cell line (a THP-1 cell line) was acquired from the Korean Cell Line Bank, and the rheumatoid arthritis patient-derived fibroblast-like synovial cells and the rheumatoid arthritis patient-derived cartilage cells were mainly acquired from patients in the Hanyang University Guri Hospital.

The human-derived macrophage cell line (a THP-1 cell line) was treated with the human shTACE/PAs-s complex for 24 hours. Also, the human-derived macrophage cell line (a THP-1 cell line), the rheumatoid arthritis patient-derived fibroblast-like synovial cells and the rheumatoid arthritis patient-derived cartilage cells were treated with the human shTACE/8D16R complex for 24 hours. Thereafter, the cells were homogeneously lysed, and only RNA was isolated using an RNeasy Lipid Tissue Mini Kit. The isolated RNA was reacted with a reverse transcriptase to synthesize cDNA complementary to 1 μg of each RNA in each group. Then, relative mRNA levels of TACE, TNF-α, TNF-receptor, MMP-1, and MMP-3 were measured with respect to the endogenous control GAPDH by RT-PCR using a Sybr Premix Ex Taq RT-PCR kit. (Human forward and reverse primers for TACE are 5'-ACCTGAAGAGCTTGTTCATC-GAG-3' [SEQ ID NO: 13] and 5'-CCATGAAGTGTTC-CGATAGATGTC-3' [SEQ ID NO: 14], respectively. Human forward and reverse primers for TNF-α are 5'-tccttcagacac-cctcaacc-3' [SEQ ID NO: 15] and 5'-cagggatcaaagctgtaggc-3' [SEQ ID NO: 16], respectively. Human forward and reverse primers for MMP-1 are 5'-AGAGCAGATGTG-GACCATGC-3' [SEQ ID NO: 17] and 5'-TTGTCCCGAT-GATCTCCCCT-3' [SEQ ID NO: 18], respectively. Human forward and reverse primers for MMP-3 are 5'-TCTATG-GACCTCCCCCTGAC-3' [SEQ ID NO: 19] and 5'-GATTT-GCGCCAAAAGTGCCT-3' [SEQ ID NO: 20], respectively. Human forward and reverse primers for TNF-receptor are 5'-tgctgtaccaagtgccacaa-3' [SEQ ID NO: 21] and 5'-ctgag-gcagtgtctgaggtg-3' [SEQ ID NO: 22], respectively. Human forward and reverse primers for GAPDH as the endogenous control are 5'-CAAGATCATCAGCAATGCC-3' [SEQ ID NO: 23] and 5'-CTGTGGTCATGAGTCCTTCC-3' [SEQ ID NO: 24], respectively.)

<Separation of CD14 Positive Cells from Synovial Fluid of Rheumatoid Arthritis Patient>

Peripheral blood mononuclear cells (PBMC) were separated from a synovial fluid taken from the knees of rheumatoid arthritis patients (provided by the Hanyang University Seoul Hospital) using a Ficoll-Paque (Amersham Bioscience AB, Ippsala, Sweden) centrifugation method. 15 mL of a patient's synovial fluid and 1×PBS were mixed at a volume ratio of 1:1 in a 50-mL tube, and 15 mL of Ficoll was carefully placed on the cells through a basal wall of the tube, centrifuged at 2,000 rpm for 20 minutes to separate a PBMC layer between a Ficoll layer and a plasma layer using a dropping pipette. The separated cells were transferred to a RPMI1640 medium, and the cells positive only for CD14 were separated using a magnetic-activated cell sorting (MACS) method. Afterward, the RPMI160 medium was used in all the procedures. MACS is a method of sorting cells specific only for specific antigens on their cell surfaces. Monocytes and macrophages specifically have CD14 on their cell surfaces, and thus only types of macrophages were obtained from the synovial fluid through the MACS. The CD14-positive monocyte/macrophage cells thus obtained were put into one well of a 6-well plate at a cell density of $1\times10^6$, and treated daily with 20 ng/mL of a macrophage colony stimulating factor (MCS-F) for 3 to 5 days. As a result, the CD14-positive PBMCs were attached to a surface of the culture plate. The attached cells were treated with the human shTACE/8D16R complex for 24 hours to determine the efficacy of the complex at mRNA and protein levels. It was confirmed through tartrate resistant acid phosphatase (TRAP) staining that such attached cells were differentiated into osteoclasts when the cells were further treated with MCS-F and a receptor activator of nuclear factor kappa-B ligand (RANKL).

<Analysis of TACE Expression Through Western Blot>

After 24 hours of the treatment with the shTACE/8D16R complex, the cell sample was lysed in a RIPA buffer including 10 mM Tris-HCl at pH 8.0, 1 mM EDTA, 140 mM NaCl, 0.1% SDS, 0.1% sodium deoxycholate, 1% Triton X-100 and, a protease inhibitor cocktail. Thereafter, the cells were cultured at 4° C. for 15 minutes, and then centrifuged at 4° C. and 14,000 g for 15 minutes. In this case, the supernatant was used as a sample. The sample was electrophoresed on SDS-PAGE, transferred to a nitrocellulose membrane, and subjected to Western blotting so that the sample was specifically bound to a TACE protein. β-actin was used as the endogenous control.

Experimental Results

1. Verification of TACE Interference of Human shTACE and Screening of Optimal Human shTACE Sequence Because a therapeutic gene RNA interference system of the present invention was used, only the TACE expression might be selectively inhibited. RNA interference is a process in which certain RNA is specifically degraded, thereby inhibiting the expression of the gene. When macrophages were treated with a human shTACE therapeutic gene alone without a lipofectamine carrier, very small amounts of genes exhibiting a negative charge due to the repulsive force of cell membranes enter the cells, resulting in little or no TACE interference effect. On the other hand, because a human shTACE therapeutic gene enters the cells due to a lipofectamine carrier, the gene can be expressed in the case of the complex, resulting in a reduced TACE mRNA level due to the TACE interference effect.

When the human-derived macrophage cell line (a THP-1 cell line) and the osteoarthritis patient-derived fibroblast-like synovial cells were treated with the shTACE/lipofectamine complex, TACE expression was inhibited due to the role of shRNA (human shTACE) which is to inhibit TACE [FIGS. 1 and 2]. The human shTACE #4 inhibited TACE expression most efficiently in the human-derived macrophage cell line (a THP-1 cell line). In the osteoarthritis patient-derived fibroblast-like synovial cells, the human shTACE #2 and #4 inhibited TACE expression. Both of the macrophages and synovial cells are cells associated with the pathology of rheumatoid arthritis. Although the degrees of inhibition of TACE expression differed in each cell, the human shTACE having an inhibitory effect in both cell types was a #4 sequence (SEQ ID NO: 5).

The next experiment was performed as follows: the human shTACE gene was used in the form of a shTACE vector including a human shTACE #4 sequence (SEQ ID NO: 10) to form a complex with a PAs-s carrier or an 8D16R carrier.

2. Preparation of Human shTACE/PAs-s Complex

To determine whether or not the human shTACE/PAs-s complex was formed and calculate a related weight thereof, electrophoresis was performed [FIG. 3]. After the total volume of the complex was adjusted, the electrophoresis was performed at 100 V on agarose gel in a 0.5×TBE buffer. When a negative charge was applied to the top of the agarose gel, a gene alone or a gene having a low weight ratio in the gene/carrier complex descended from the top of the agarose gel due to the repulsive force, but the gene no longer descended any more because the gene was hung on the top of the agarose gel when the gene normally formed a complex with the carrier. After 1 µg of human shTACE was mixed with varying amounts (0.5, 1, 2, 3, 4 µg) of the PAs-s carrier, it was confirmed by electrophoresis whether or not the shTACE/PAs-s complex was formed. The formation of the shTACE/PAs-s complex was started when the weight ratio of the gene to the carrier was greater than 1 [FIG. 3]. In the agarose gel electrophoresis, white bands indicate the gene (indicated by the arrows). Bands were observed in the group treated with the gene alone (ND, Naked DNA) and the group (WW 0.5) in which the genes formed a complex with a low concentration of the carrier at the weight ratio of 0.5 (PAs-s/shTACE=0.5). From these facts, it was confirmed that the gene was observed in the form of a band because the gene did not normally form a complex due to a low concentration of the carrier. Also, when the weight ratio of the human shTACE/PAs-s complex was 2 (PAs-s/shTACE=2), the complex had a high positive value of zeta potential and appropriate size and PDI [FIG. 4, 5, 6]. The average particle size and average PDI value of the complex were considered to be close to approximately 100 to 220 nm and 0.1 to 0.2, respectively. To check the shape of the human shTACE/PAs-s complex with the naked eye, energy-filtered transmission microscopy (EF-TEM) was performed. The helical structure of DNA was able to be observed when only the human shTACE therapeutic gene without any PAs-s carrier was measured by EF-TEM, whereas a spherical shape having a diameter of 100 to 200 nm was able to be observed in the case of the shTACE/PAs-s complex in which the complex was formed with the PAs-s carrier [FIG. 7].

Non-toxicity of the gene/carrier complex was determined with respect to the degree of cell apoptosis using a fluorescence-activated cell sorting (FACS) assay. The cells were treated with the human shTACE/PAs-s complex for 24 hours. Thereafter, the cells of each group were harvested, and treated with phycoerythrin (PE)-annexin V and 7-amino-actinomycin (7-AAD). Upon cell apoptosis, the position of phospholipid phosphatidylserine (PS) was changed from the inside to outside of a cell membrane, where annexin V reacts with the PS. Thus, when the cells react with annexin V, this means early-stage cell apoptosis. Also, because dead cells (or damaged cells) are known to be permeable to 7-AAD, when the cells react with 7-AAD, this means late-stage cell apoptosis. In FIG. 8, Quarter 4 (Q4) means early-stage cell apoptosis, Quarter 1 (Q1) means late-stage cell apoptosis, and Quarter 2 (Q2) means cell apoptosis. A degree of toxicity of the gene/carrier complex was measured based on the ratio of distribution corresponding to the Q2 meaning cell apoptosis in the entire cell distribution.

The group treated with the human shTACE/PAs-s complex had a similar pattern of cell apoptosis, compared to the untreated control and the group treated with the gene alone (Naked shTACE), which indirectly indicated that the complex was not toxic [FIG. 8]. On the other hand, a high degree of Q2 distribution was observed in the human shTACE/PEI complex in which a polyethyleneimine carrier known to be toxic was used.

A degree of intracellular delivery of the gene by the PAs-s carrier was measured using a fluorescence-activated cell sorting (FACS) assay. A Cy5 fluorophore-linked gene (Cy5-shTACE) was mixed with a PAs-s carrier, and human-derived macrophages (THP-1 cell line) were then treated with the resulting complex. When the Cy5 fluorophore-linked gene (Cy5-shTACE) entered the human-derived macrophages (THP-1 cell line), a positive result for Cy5 fluorescence was obtained upon the FACS analysis. When the cells were treated with the Cy5 fluorophore-linked gene alone (Cy5-shTACE), almost the same results were obtained, compared to the untreated control. However, when the gene was mixed with the PAs-s carrier and the cells were treated with the complex, a Cy5 fluorescence value was measured because the Cy5 fluorophore-linked gene (Cy5-shTACE) entered the cells. Also, when this level was quantitatively analyzed, an MFI value increased by approximately 40 times, compared to the group in which the cells were treated with the Cy5 fluorophore-linked gene alone (Cy5-shTACE) [FIG. 9].

3. Confirmation of Anti-Inflammatory Effect of Human shTACE/PAs-s Complex

When human-derived macrophages (THP-1 cell line) were treated with the shTACE/PAs-s complex, the TACE expression was inhibited due to the role of shRNA (shTACE) which is to inhibit TACE [FIG. 10]. Because the therapeutic gene RNA interference system of the present invention was used, only TACE expression might be selectively regulated. RNA interference is a process in which certain RNA is specifically degraded, thereby inhibiting the expression of the gene. When the macrophages were treated with shTACE alone without a PAs-s carrier, very small amounts of genes exhibiting a negative charge due to the repulsive force of cell membranes enter the cells, resulting in little or no TACE interference effect. On the other hand, because the shTACE gene enters the cells due to the PAs-s carrier, the gene can be expressed in the case of the complex, resulting in a reduced TACE mRNA level due to the TACE interference effect.

TACE is increasingly expressed in various inflammatory diseases to induce the release of a main inflammatory mediator TNF-α, resulting in an aggravated inflammatory condition. Therefore, when TACE expression is inhibited, it is possible to prevent and treat rheumatoid arthritis. When the human shTACE targeting TACE was treated with the complex which had been formed with the carrier, an mRNA level of an inflammatory cytokine TNF-α was reduced in the human-derived macrophages (THP-1 cell line) [FIG. 11]. In this way, the anti-inflammatory effect of the shTACE/PAs-s complex in the macrophages was verified. Also, when the human-derived macrophages (THP-1 cell line) were treated with the complex, a TNF-receptor mRNA level was also reduced. In this way, it was judged that an inflammatory signaling pathway mediated by the inflammatory cytokine TNF-α was also weakened. The anti-inflammatory effect was indirectly confirmed at an in vitro cellular level based on the weakened TNF-α inflammatory signals [FIG. 12].

4. Preparation of Human shTACE/8D16R Complex

To determine whether or not the human shTACE/8D16R complex was formed and calculate a related weight thereof, electrophoresis was performed [FIG. 13]. After the total volume of the complex was adjusted, the electrophoresis was performed at 100 V on agarose gel in a 0.5×TBE buffer. When a negative charge was applied to the top of the agarose gel, a gene alone or a gene having a low weight ratio in the gene/carrier complex descended from the top of the agarose gel due to the repulsive force, but the gene no longer descended any more because the gene was hung on the top of the agarose gel when the gene normally formed a complex with the carrier. After 1 μg of human shTACE was mixed with varying amounts (1, 2, 3, 4, 6 μg) of the 8D16R carrier, it was confirmed by electrophoresis whether or not the shTACE/8D16R complex was formed. The formation of the shTACE/8D16R complex was started when the weight ratio of the gene to the carrier was greater than 1 [FIG. 13]. In the agarose gel electrophoresis, white bands indicate the gene (indicated by the arrows). A band was observed in the group treated with the gene alone (ND, Naked DNA), but no bands were observed in the other groups in which the cells were treated with the varying amounts of the shTACE/8D16R complex. From these facts, it was confirmed that the band was not observed in the shTACE/8D16R complex having a weight ratio of 1 or more because the complex was normally formed. Also, when the weight ratio of the human shTACE/8D16R complex was 4 (8D16R/shTACE=4), the complex had a high positive value of zeta potential and appropriate size and PDI [FIG. 14, 15, 16]. The average particle size and average PDI value of the complex were considered to be close to approximately 150 to 220 nm and 0.1 to 0.2, respectively. To check the shape of the human shTACE/8D16R complex with the naked eye, energy-filtered transmission microscopy (EF-TEM) was performed. The helical structure of DNA was able to be observed when only the human shTACE without any 8D16R carrier was measured by EF-TEM, whereas a spherical shape having a diameter of 100 to 200 nm was able to be observed in the case of the shTACE/8D16R complex in which the complex was formed with the 8D16R carrier [FIG. 17].

Non-toxicity of the gene/carrier complex was determined with respect to the degree of cell apoptosis using a fluorescence-activated cell sorting (FACS) assay. The cells were treated with the human shTACE/8D16R complex for 24 hours. Thereafter, the cells of each group were harvested, and treated with phycoerythrin (PE)-annexin V and 7-amino-actinomycin (7-AAD). Upon cell apoptosis, the position of phospholipid phosphatidylserine (PS) is changed from the inside to outside of a cell membrane, where annexin V reacts with the PS. Thus, when the cells react with annexin V, this means early-stage cell apoptosis. Also, because dead cells (or damaged cells) are known to be permeable to 7-AAD, when the cells react with 7-AAD, this means late-stage cell apoptosis. In FIG. 8, Quarter 4 (Q4) means early-stage cell apoptosis, Quarter 1 (Q1) means late-stage cell apoptosis, and Quarter 2 (Q2) means cell apoptosis. A degree of toxicity of the gene/carrier complex was measured based on the ratio of distribution corresponding to the Q2 meaning cell apoptosis in the entire cell distribution. The group treated with the human shTACE/8D16R complex had a similar pattern of cell apoptosis, compared to the untreated control and the group treated with the gene alone (Naked shTACE), which indirectly indicated that the complex was not toxic [FIG. 8]. On the other hand, a high degree of Q2 distribution was observed in the human shTACE/PEI complex in which a polyethyleneimine carrier known to be toxic was used.

A degree of intracellular delivery of the gene by the 8D16R carrier was measured using a fluorescence-activated cell sorting (FACS) assay. A Cy5 fluorophore-linked gene (Cy5-shTACE) was mixed with an 8D16R carrier, and human-derived macrophages (THP-1 cell line) were then treated with the resulting complex. When the Cy5 fluorophore-linked gene (Cy5-shTACE) entered the human-derived macrophages (THP-1 cell line), a positive result for Cy5 fluorescence was obtained upon the FACS analysis. When the cells were treated with the Cy5 fluorophore-linked gene alone (Cy5-shTACE), almost the same results were obtained, compared to the untreated control. However, when the gene was mixed with the 8D16R carrier and the cells were treated with the complex, a Cy5 fluorescence value was measured because the Cy5 fluorophore-linked gene (Cy5-shTACE) entered the cells. Also, when this level was quantitatively analyzed, an MFI value increased by approximately 120 times, compared to the group in which the cells were treated with the Cy5 fluorophore-linked gene alone (Cy5-shTACE) [FIG. 18].

5. Verification of Therapeutic Effect of Human shTACE/8D16R Complex on Rheumatoid Arthritis When a human-derived macrophage cell line (THP-1 cell line) was treated with the human shTACE/8D16R complex, TACE mRNA expression was inhibited due to the role of human shTACE which is to inhibit TACE expression [FIG. 19]. As the TACE was inhibited, TNF-α mRNA which is an inflammatory cytokine was inhibited in the shTACE/8D16R complex-treated group [FIG. 20]. That is, it was verified that human shTACE formed with a complex with an 8D16R peptide carrier, and thus had a therapeutic effect even in a human cell line.

Fibroblast-like synovial cells derived from rheumatoid arthritis patients was obtained, and cultured under conditions of 37° C. and 5% $CO_2$. After the cell culture, when the cells were treated with the shTACE/8D16R complex for 24 hours, TACE mRNA and TNF-α mRNA were inhibited due to the role of shRNA (Human shTACE) which is to inhibit TACE [FIG. 21, 22].

When the cells were treated with the shTACE/8D16R complex of the present invention, the expression of the main target TACE and the inflammatory cytokine TNF-α was inhibited, and the expression of matrix metalloproteinases (MMPs) was also inhibited [FIG. 23, 24]. When MMP expression increases, tissues such as collagen, and the like are decomposed, resulting in aggravated rheumatoid arthritis. Likewise, it was confirmed that, when cartilage cells derived from rheumatoid arthritis patients were also treated with the shTACE/8D16R complex of the present invention, TACE mRNA, TNF-α mRNA, and MMP-1 mRNA were inhibited [FIG. 25, 26, 27]. Also, it was confirmed that the shTACE/8D16R complex had a superior inhibitory effect when the cells were treated with the complex for 24 hours, compared to when the cells were treated with the complex for 6 hours.

Cells positive only for CD14 were isolated from the synovial fluid of rheumatoid arthritis patients using a magnetic-activated cell sorting (MACS) method. The cells positive for CD14 belong to monocyte and macrophage cell lines. The isolated cells were treated with MCS-F so that the cells were attached to a well plate. Thereafter, the cells were treated with the shTACE/8D16R complex for 24 hours. The group in which the cells were treated at 1.5 μg per well on a genetic basis was named a complex low concentration group (an shTACE/8D16R complex low concentration group), and the group in which the cells were treated at 3 μg per well was named a complex high concentration group (a shTACE/8D16R complex high concentration group). It was confirmed that, when the cells were treated with the shTACE/8D16R complex, TACE mRNA, TNF-α mRNA, and MMP-1 mRNA were inhibited [FIG. 28, 29, 30].

The shTACE/8D16R complex reduced TACE expression at a protein level in all the fibroblast-like synovial cells, cartilage cells, and macrophages (CD14 positive macrophages) derived from rheumatoid arthritis patients [FIG. 31, 32, 33]. As a result, it can be seen that an anti-inflammatory effect was observed in the various cells associated with rheumatoid arthritis. This is an important mechanism for rheumatoid arthritis, which is mainly characterized by a sustained inflammatory response in the synovial joint. Also, the inhibition of TACE expression leads to the inhibition of MMP expression. As rheumatoid arthritis develops, an anti-inflammatory effect and a joint damage-preventing effect were all verified by inhibiting MMP which serves to destroy collagen, attack joints, and the like.

When the gene/carrier complex according to the present invention is injected into the body, a therapeutic gene can be efficiently delivered, and as a result, TACE expression can be effectively inhibited. Therefore, the complex of the present invention may have an excellent effect in the prevention or treatment of inflammatory diseases.

In particular, the gene/carrier complex according to the present invention also exhibited an anti-inflammatory effect in all the human-derived macrophage cell line and the fibroblast-like synovial cells, cartilage cells, and macrophages (CD14 positive monocyte/macrophages) derived from rheumatoid arthritis patients. That is, the clinical applicability of this gene therapy agent for treatment of rheumatoid arthritis was verified through patient-derived substance-based studies.

While the invention has been shown and described with reference to certain exemplary embodiments thereof, it will be understood by those skilled in the art that various changes in form and details may be made therein without departing from the spirit and scope of the invention as defined by the appended claims.

What is claimed is:

1. A gene/carrier complex comprising:
   one or more shRNAs selected from the group consisting of SEQ ID NOS: 2 to 5, which inhibit expression of a tumor necrosis factor-alpha converting enzyme (a TNF-α converting enzyme, TACE); and
   a nonviral gene carrier,
   wherein the nonviral gene carrier comprises a trifluoroacetic acid (TFA) salt of poly(oligo-aspartic acid)(oligo-arginine).

2. The gene/carrier complex according to claim 1, wherein the poly(oligo-aspartic acid)(oligo-arginine) comprises cysteines at both ends thereof.

3. The gene/carrier complex according to claim 1, wherein the poly(oligo-aspartic acid)(oligo-arginine) is a Cys-(8×Asp)-(16×Arg)-Cys peptide, wherein the peptide comprises cysteines at both ends thereof and is composed of an eight-aspartic acid oligomer and a sixteen-arginine oligomer.

4. The gene/carrier complex according to claim 1, wherein TACE shRNA and the gene carrier are present in a weight ratio of 1:1.5 to 8.

5. The gene/carrier complex according to claim 1, wherein the shRNA is in the form such that it is contained in a plasmid vector.

6. The gene/carrier complex according to claim 5, wherein the plasmid vector containing the shRNA has at least one base sequence selected from the group consisting of SEQ ID NOS: 7 to 10.

7. A method of preparing a gene/carrier complex, the method comprising mixing and incubating one or more shRNAs selected from the group consisting of SEQ ID NOS: 2 to 5, which inhibit expression of a tumor necrosis factor-alpha converting enzyme (TNF-α converting enzyme, TACE), and a nonviral carrier,
   wherein the nonviral gene carrier comprises a trifluoroacetic acid (TFA) salt of poly(oligo-aspartic acid) (oligo-arginine).

8. The method according to claim 7, wherein the incubation is performed at 20 to 40° C. for 20 to 40 minutes.

9. The method according to claim 7, wherein the poly (oligo-aspartic acid)(oligo-arginine) comprises cysteines at both ends thereof.

10. The method according to claim 7, wherein the poly (oligo-aspartic acid)(oligo-arginine) is a Cys-(8×Asp)-(16× Arg)-Cys peptide, wherein the peptide comprises cysteines at both ends thereof and is composed of an eight-aspartic acid oligomer and a sixteen-arginine oligomer.

11. The method according to claim 7, wherein the shRNA is in the form such that it is contained in a plasmid vector.

12. The method according to claim 7, wherein the plasmid vector containing the shRNA has at least one base sequence selected from the group consisting of SEQ ID NOS: 7 to 10.

13. A method of treating rheumatoid arthritis, comprising administering an effective amount of the gene/carrier complex according to claim 1 as an active ingredient to a subject.

14. The method according to claim 13, wherein the complex is administered through oral, aerosol, buccal, epidermal, intradermal, inhalation, intramuscular, intranasal, intraocular, intrapulmonary, intravenous, intraperitoneal, nasal, ocular, oral, ear, injection, patch, subcutaneous, hypoglossal, topical or percutaneous routes.

* * * * *

SEQUENCE LISTING

<160> NUMBER OF SEQ ID NOS: 24

<210> SEQ ID NO 1
<211> LENGTH: 58
<212> TYPE: DNA
<213> ORGANISM: Artificial Sequence
<220> FEATURE:
<223> OTHER INFORMATION: mouse shTACE

<400> SEQUENCE: 1
gatccgacac ctgctgcaat agtgatcaag agtcactatt gcagcaggtg ttttttg       58

<210> SEQ ID NO 2
<211> LENGTH: 62
<212> TYPE: DNA
<213> ORGANISM: Artificial Sequence
<220> FEATURE:
<223> OTHER INFORMATION: human shTACE #1

<400> SEQUENCE: 2
gatccgggag atttgttaat gataccatca agagtggtat cattaacaaa tctccttttt    60
tg                                                                    62

<210> SEQ ID NO 3
<211> LENGTH: 62
<212> TYPE: DNA
<213> ORGANISM: Artificial Sequence
<220> FEATURE:
<223> OTHER INFORMATION: human shTACE #2

<400> SEQUENCE: 3
gatccgcctg gttacaactc atgaatttca agagaattca tgagttgtaa ccaggttttt    60
tg                                                                    62

<210> SEQ ID NO 4
<211> LENGTH: 62
<212> TYPE: DNA
<213> ORGANISM: Artificial Sequence
<220> FEATURE:
<223> OTHER INFORMATION: human shTACE #3

<400> SEQUENCE: 4

```
gatccgggcg attaatgcta cttgcaatca agagttgcaa gtagcattaa tcgcctttt    60 tg                                                                 62

<210> SEQ ID NO 5
<211> LENGTH: 62
<212> TYPE: DNA
<213> ORGANISM: Artificial Sequence
<220> FEATURE:
<223> OTHER INFORMATION: human shTACE #4

<400> SEQUENCE: 5
gatccgccat tgtgtggata agaaatttca agagaatttc ttatccacac aatggttttt   60
tg                                                                 62

<210> SEQ ID NO 6
<211> LENGTH: 6669
<212> TYPE: DNA
<213> ORGANISM: Artificial Sequence
<220> FEATURE:
<223> OTHER INFORMATION: mouse shTACE vector

<400> SEQUENCE: 6
gaattcgcgg ccctagcttg ggatctttgt gaaggaacct tacttctgtg gtgtgacata    60
attggacaaa ctacctacag agatttaaag ctctaaggta aatataaaat ttttaagtgt   120
ataatgtgtt aaactagctg catatgcttg ctgcttgaga gttttgctta ctgagtatga   180
tttatgaaaa tattatacac aggagctagt gattctaatt gtttgtgtat tttagattca   240
cagtcccaag gctcatttca ggcccctcag tcctcacagt ctgttcatga tcataatcag   300
ccataccaca tttgtagagg ttttacttgc tttaaaaaac ctcccacacc tccccctgaa   360
cctgaaacat aaaatgaatg caattgttgt tgttaacttg tttattgcag cttataatgg   420
ttacaaataa agcaatagca tcacaaattt cacaaataaa gcatttttt cactgcattc    480 tagttgtggt ttgtccaaac tcatcaatgt atcttatcat gtctggatcg atcctgcatt   540
aatgaatcgg ccaacgcgcg gggagaggcg gtttgcgtat tggctggcgt aatagcgaag   600
aggcccgcac cgatcgccct tcccaacagt tgcgcagcct gaatggcgaa tgggacgcgc   660
cctgtagcgg cgcattaagc gcggcgggtg tggtggttac gcgcagcgtg accgctacac   720
ttgccagcgc cctagcgccc gctcctttcg ctttcttccc ttcctttctc gccacgttcg   780
ccggctttcc ccgtcaagct ctaaatcggg ggctcccttt agggttccga tttagtgctt   840
tacggcacct cgaccccaaa aaacttgatt agggtgatgg ttcacgtagt gggccatcgc   900
cctgatagac ggtttttcgc cctttgacgt tggagtccac gttctttaat agtggactct   960
tgttccaaac tggaacaaca ctcaacccta tctcggtcta ttcttttgat ttataaggga  1020
ttttgccgat ttcggcctat tggttaaaaa atgagctgat ttaacaaata tttaacgcga  1080
attttaacaa aatattaacg tttacaattt cgcctgatgc ggtattttct ccttacgcat  1140
ctgtgcggta tttcacaccg catacgcgga tctgcgcagc accatggcct gaaataacct  1200
ctgaaagagg aacttggtta ggaaccttct gaggcggaaa gaaccagctg tggaatgtgt  1260
gtcagttagg gtgtggaaag tccccaggct ccccagcagg cagaagtatg caaagcatgc  1320
atctcaatta gtcagcaacc aggtgtggaa agtccccagg ctccccagca ggcagaagta  1380
tgcaaagcat gcatctcaat tagtcagcaa ccatagtccc gcccctaact ccgcccatcc  1440
cgcccctaac tccgcccagt tccgcccatt ctccgcccca tggctgacta attttttta   1500 tttatgcaga ggccgaggcc gcctcggcct ctgagctatt ccagaagtag tgaggaggct  1560
```

```
tttttggagg cctaggcttt tgcaaaaagc ttgattcttc tgacacaaca gtctcgaact    1620
taaggctaga gccaccatga ccgagtacaa gcccacggtg cgcctcgcca cccgcgacga    1680
cgtccccagg gccgtacgca ccctcgccgc cgcgttcgcc gactacaccg ccacgcgcca    1740
caccgtcgat ccggaccgcc acatcgagcg ggtcaccgag ctgcaagaac tcttcctcac    1800
gcgcgtcggg ctcgacatcg gcaaggtgtg ggtcgcggac gacggcgccg cggtggcggt    1860
ctggaccacg ccggagagcg tcgaagcggg ggcggtgttc gccgagatcg gcccgcgcat    1920
ggccgagttg agcggttccc ggctggccgc gcagcaacag atggaaggcc tcctggcgcc    1980
gcaccggccc aaggagcccg cgtggttcct ggccaccgtc ggcgtctcgc ccgaccacca    2040
gggcaagggt ctgggcagcg ccgtcgtgct ccccggagtg gaggcggccg agcgcgccgg    2100
ggtgcccgcc ttcctggaga cctccgcgcc ccgcaacctc cccttctacg agcggctcgg    2160
cttcaccgtc accgccgacg tcgaggtgcc cgaaggaccg cgaacctggt gcatgacccg    2220
caagcccggt gcctgagttt aacgaaatga ccgaccaagc gacgcccaac ctgccatcac    2280
gatggccgca ataaaatatc tttattttca ttacatctgt gtgttggttt tttgtgtgga    2340
tcgatagcga taaggatcga tccgcgcatg gtgcactctc agtacaatct gctctgatgc    2400
cgcatagtta agccagcccc gacacccgcc aacacccgct gacgcgccct gacgggcttg    2460
tctgctcccg gcatccgctt acagacaagc tgtgaccgtc tccgggagct gcatgtgtca    2520
gaggttttca ccgtcatcac cgaaacgcgc gagacgaaag ggcctcgtga tacgcctatt    2580
tttataggtt aatgtcatga taataatggt ttcttagacg tcaggtggca cttttcgggg    2640
aaatgtgcgc ggaaccccta tttgtttatt tttctaaata cattcaaata tgtatccgct    2700
catgagacaa taaccctgat aaatgcttca ataatattga aaaggaaga gtatgagtat    2760 tcaacatttc cgtgtcgccc ttattccctt ttttgcggca ttttgccttc ctgtttttgc    2820
tcacccagaa acgctggtga agtaaaaga tgctgaagat cagttgggtg cacgagtggg    2880
ttacatcgaa ctggatctca acagcggtaa gatccttgag agttttcgcc ccgaagaccg    2940
ttttccaatg atgagcactt ttaaagttct gctatgtggc gcggtattat cccgtattga    3000
cgccgggcaa gagcaactcg gtcgccgcat acactattct cagaatgact tggttgagta    3060
ctcaccagtc acagaaaagc atcttacgga tggcatgaca gtaagagaat tatgcagtgc    3120
tgccataacc atgagtgata acactgcggc caacttactt ctgacaacga tcggaggacc    3180
gaaggagcta accgcttttt tgcacaacat gggggatcat gtaactcgcc ttgatcgttg    3240
ggaaccggag ctgaatgaag ccataccaaa cgacgagcgt gacaccacga tgcctgtagc    3300
aatggcaaca acgttgcgca aactattaac tggcgaacta cttactctag cttcccggca    3360
acaattaata gactggatgg aggcggataa agttgcagga ccacttctgc gctcggccct    3420
tccggctggc tggtttattg ctgataaatc tggagccggt gagcgtgggt ctcgcggtat    3480
cattgcagca ctggggccag atggtaagcc ctcccgtatc gtagttatct acacgacggg    3540
gagtcaggca actatggatg aacgaaatag acagatcgct gagataggtg cctcactgat    3600
taagcattgg taactgtcag accaagttta ctcatatata ctttagattg atttaaaact    3660
tcatttttaa tttaaaagga tctaggtgaa gatcctttt gataatctca tgaccaaaat    3720
cccttaacgt gagttttcgt tccactgagc gtcagacccc gtagaaaaga tcaaaggatc    3780
ttcttgagat cctttttttc tgcgcgtaat ctgctgcttg caaacaaaaa aaccaccgct    3840
accagcggtg gtttgtttgc cggatcaaga gctaccaact cttttccga aggtaactgg    3900
```

```
cttcagcaga gcgcagatac caaatactgt ccttctagtg tagccgtagt taggccacca   3960
cttcaagaac tctgtagcac cgcctacata cctcgctctg ctaatcctgt taccagtggc   4020
tgctgccagt ggcgataagt cgtgtcttac cgggttggac tcaagacgat agttaccgga   4080
taaggcgcag cggtcgggct gaacgggggg ttcgtgcaca cagcccagct tggagcgaac   4140
gacctacacc gaactgagat acctacagcg tgagcattga gaaagcgcca cgcttcccga   4200
agggagaaag gcggacaggt atccggtaag cggcagggtc ggaacaggag agcgcacgag   4260
ggagcttcca gggggaaacg cctggtatct ttatagtcct gtcgggtttc gccacctctg   4320
acttgagcgt cgattttgt gatgctcgtc aggggggcgg agcctatgga aaaacgccag   4380
caacgcggcc ttttacggt tcctggcctt ttgctggcct tttgctcaca tgttctttcc   4440
tgcgttatcc cctgattctg tggataaccg tattaccgcc tttgagtgag ctgataccgc   4500
tcgccgcagc cgaacgaccg agcgcagcga gtcagtgagc gaggaagcgg aagagcgccc   4560
aatacgcaaa ccgcctctcc ccgcgcgttg gccgattcat taatgcagag cttgcaattc   4620
gcgcgttttt caatattatt gaagcattta tcagggttat tgtctcatga gcggatacat   4680
atttgaatgt atttagaaaa ataaacaaat aggggttccg cgcacatttc cccgaaaagt   4740
gccacctgac gtctaagaaa ccattattat catgacatta acctataaaa ataggcgtag   4800
tacgaggccc tttcactcat tagatgcatg tcgttacata acttacggta aatggcccgc   4860
ctggctgacc gcccaacgac ccccgcccat tgacgtcaat aatgacgtat gttcccatag   4920
taacgccaat agggactttc cattgacgtc aatgggtgga gtatttacgg taaactgccc   4980
acttggcagt acatcaagtg tatcatatgc caagtacgcc ccctattgac gtcaatgacg   5040
gtaaatggcc cgcctggcat tatgcccagt acatgacctt atgggacttt cctacttggc   5100
agtacatcta cgtattagtc atcgctatta ccatggtgat gcggttttgg cagtacatca   5160
atgggcgtgg atagcggttt gactcacggg gatttccaag tctccacccc attgacgtca   5220
atgggagttt gttttggcac caaaatcaac gggactttcc aaaatgtcgt aacaactccg   5280
ccccattgac gcaaatgggc ggtaggcgtg tacggtggga ggtctatata agcagagctc   5340
gtttagtgaa ccgtcagatc gcctggagac gccatccacg ctgttttgac ctccatagaa   5400
gacaccggga ccgatccagc ctccggactc tagcctaggc gcgggaccat gtccggcttg   5460
aacgacatct tcgaggccca gaagatcgag tggcacgagg aaaagcttcg aaccatggtg   5520
agcaagggcg aggagctgtt caccggggtg gtgcccatcc tggtcgagct ggacggcgac   5580
gtaaacggcc acaagttcag cgtgtccggc gagggcgagg gcgatgccac ctacggcaag   5640
ctgaccctga agttcatctg caccaccggc aagctgcccg tgccctggcc caccctcgtg   5700
accaccctga cctacggcgt gcagtgcttc agccgctacc ccgaccacat gaagcagcac   5760
gacttcttca gtccgccat gcccgaaggc tacgtccagg agcgcaccat cttcttcaag   5820
gacgacggca actacaagac ccgcgccgag gtgaagttcg agggcgacac cctggtgaac   5880
cgcatcgagc tgaagggcat cgacttcaag gaggacggca acatcctggg gcacaagctg   5940
gagtacaact acaacagcca caacgtctat atcatggccg acaagcagaa gaacggcatc   6000
aaggtgaact tcaagatccg ccacaacatc gaggacggca gcgtgcagct cgccgaccac   6060
taccagcaga acacccccat cggcgacggc cccgtgctgc tgcccgacaa ccactacctg   6120
agcacccagt ccgccctgag caaagacccc aacgagaagc gcgatcacat ggtcctgctg   6180
gagttcgtga ccgccgccgg gatcactctc ggcatggacg agctgtacaa gtagctcgag   6240 tgcggccca aataatgatt ttattttgac tgatagtgac ctgttcgttg caacaaattg   6300
```

-continued

| | |
|---|---|
| atgagcaatg cttttttata atgccaactt tgtacaaaaa agcaggctgc gatcgctcgg | 6360 |
| gcaggaagag ggcctatttc ccatgattcc ttcatatttg catatacgat acaaggctgt | 6420 |
| tagagagata attagaatta atttgactgt aaacacaaag atattagtac aaaatacgtg | 6480 |
| acgtagaaag taataatttc ttgggtagtt tgcagtttta aaattatgtt ttaaaatgga | 6540 |
| ctatcatatg cttaccgtaa cttgaaagta tttcgatttc ttgggtttat atatcttgtg | 6600 |
| gaaaggacga ggatccgaca cctgctgcaa tagtgatcaa gagtcactat tgcagcaggt | 6660 |
| gtttttttg | 6669 |

<210> SEQ ID NO 7
<211> LENGTH: 6673
<212> TYPE: DNA
<213> ORGANISM: Artificial Sequence
<220> FEATURE:
<223> OTHER INFORMATION: human shTACE #1 vector
<400> SEQUENCE: 7

| | |
|---|---|
| gaattcgcgg ccctagcttg ggatctttgt gaaggaacct tacttctgtg gtgtgacata | 60 |
| attggacaaa ctacctacag agatttaaag ctctaaggta aatataaaat ttttaagtgt | 120 |
| ataatgtgtt aaactagctg catatgcttg ctgcttgaga gttttgctta ctgagtatga | 180 |
| tttatgaaaa tattatacac aggagctagt gattctaatt gtttgtgtat tttagattca | 240 |
| cagtcccaag gctcatttca ggcccctcag tcctcacagt ctgttcatga tcataatcag | 300 |
| ccataccaca tttgtagagg ttttacttgc tttaaaaaac ctcccacacc tccccctgaa | 360 |
| cctgaaacat aaaatgaatg caattgttgt tgttaacttg tttattgcag cttataatgg | 420 |
| ttacaaataa agcaatagca tcacaaattt cacaaataaa gcattttttt cactgcattc | 480 |
| tagttgtggt ttgtccaaac tcatcaatgt atcttatcat gtctggatcg atcctgcatt | 540 |
| aatgaatcgg ccaacgcgcg gggagaggcg gtttgcgtat tggctggcgt aatagcgaag | 600 |
| aggcccgcac cgatcgccct tcccaacagt tgcgcagcct gaatggcgaa tgggacgcgc | 660 |
| cctgtagcgg cgcattaagc gcggcgggtg tggtggttac gcgcagcgtg accgctacac | 720 |
| ttgccagcgc cctagcgccc gctcctttcg ctttcttccc ttcctttctc gccacgttcg | 780 |
| ccggctttcc ccgtcaagct ctaaatcggg ggctcccttt agggttccga tttagtgctt | 840 |
| tacggcacct cgaccccaaa aaacttgatt agggtgatgg ttcacgtagt gggccatcgc | 900 |
| cctgatagac ggtttttcgc cctttgacgt tggagtccac gttctttaat agtggactct | 960 |
| tgttccaaac tggaacaaca ctcaacccta tctcggtcta ttcttttgat ttataaggga | 1020 |
| ttttgccgat ttcggcctat tggttaaaaa atgagctgat ttaacaaata tttaacgcga | 1080 |
| attttaacaa aatattaacg tttacaattt cgcctgatgc ggtattttct ccttacgcat | 1140 |
| ctgtgcggta tttcacaccg catacgcgga tctgcgcagc accatggcct gaaataacct | 1200 |
| ctgaaagagg aacttggtta ggaaccttct gaggcgaaa gaaccagctg tggaatgtgt | 1260 |
| gtcagttagg gtgtggaaag tccccaggct ccccagcagg cagaagtatg caaagcatgc | 1320 |
| atctcaatta gtcagcaacc aggtgtggaa agtcccaggg ctccccagca ggcagaagta | 1380 |
| tgcaaagcat gcatctcaat tagtcagcaa ccatagtccc gcccctaact ccgcccatcc | 1440 |
| cgcccctaac tccgcccagt tccgcccatt ctccgcccca tggctgacta atttttttta | 1500 |
| tttatgcaga ggccgaggcc gcctcggcct ctgagctatt ccagaagtag tgaggaggct | 1560 |
| tttttggagg cctaggcttt tgcaaaaagc ttgattcttc tgacacaaca gtctcgaact | 1620 |

```
taaggctaga gccaccatga ccgagtacaa gcccacggtg cgcctcgcca cccgcgacga    1680
cgtccccagg gccgtacgca ccctcgccgc cgcgttcgcc gactaccccg ccacgcgcca    1740
caccgtcgat ccggaccgcc acatcgagcg ggtcaccgag ctgcaagaac tcttcctcac    1800
gcgcgtcggg ctcgacatcg gcaaggtgtg ggtcgcggac gacggcgccg cggtggcggt    1860
ctggaccacg ccggagagcg tcgaagcggg ggcggtgttc gccgagatcg gcccgcgcat    1920
ggccgagttg agcggttccc ggctggccgc gcagcaacag atggaaggcc tcctggcgcc    1980
gcaccggccc aaggagcccg cgtggttcct ggccaccgtc ggcgtctcgc ccgaccacca    2040
gggcaagggt ctgggcagcg ccgtcgtgct ccccggagtg gaggcggccg agcgcgccgg    2100
ggtgcccgcc ttcctggaga cctccgcgcc ccgcaacctc cccttctacg agcggctcgg    2160
cttcaccgtc accgccgacg tcgaggtgcc cgaaggaccg cgaacctggt gcatgacccg    2220
caagcccggt gcctgagttt aacgaaatga ccgaccaagc gacgcccaac ctgccatcac    2280
gatggccgca ataaaatatc tttattttca ttacatctgt gtgttggttt tttgtgtgga    2340
tcgatagcga taaggatcga tccgcgcatg gtgcactctc agtacaatct gctctgatgc    2400
cgcatagtta agccagcccc gacacccgcc aacacccgct gacgcgccct gacgggcttg    2460
tctgctcccg gcatccgctt acagacaagc tgtgaccgtc tccgggagct gcatgtgtca    2520
gaggttttca ccgtcatcac cgaaacgcgc gagacgaaag gcctcgtga tacgcctatt    2580 tttataggtt aatgtcatga taataatggt tccttagacg tcaggtggca cttttcgggg    2640
aaatgtgcgc ggaacccta tttgtttatt tttctaaata cattcaaata tgtatccgct    2700
catgagacaa taaccctgat aaatgcttca ataatattga aaaggaaga gtatgagtat    2760 tcaacatttc cgtgtcgccc ttattccctt ttttgcggca ttttgccttc ctgttttttgc    2820 tcacccagaa acgctggtga agtaaaaga tgctgaagat cagttgggtg cacgagtggg    2880
ttacatcgaa ctggatctca acagcggtaa gatccttgag agttttcgcc ccgaagaccg    2940
ttttccaatg atgagcactt ttaaagttct gctatgtggc gcggtattat cccgtattga    3000
cgccgggcaa gagcaactcg gtcgccgcat acactattct cagaatgact tggttgagta    3060
ctcaccagtc acagaaaagc atcttacgga tggcatgaca gtaagagaat tatgcagtgc    3120
tgccataacc atgagtgata acactgcggc caacttactt ctgacaacga tcggaggacc    3180
gaaggagcta accgcttttt tgcacaacat ggggatcat gtaactcgcc ttgatcgttg    3240
ggaaccggag ctgaatgaag ccataccaaa cgacgagcgt gacaccacga tgcctgtagc    3300
aatggcaaca acgttgcgca aactattaac tggcgaacta cttactctag cttcccggca    3360
acaattaata gactggatgg aggcggataa agttgcagga ccacttctgc gctcggccct    3420
tccggctggc tggtttattg ctgataaatc tggagccggt gagcgtgggt ctcgcggtat    3480
cattgcagca ctggggccag atggtaagcc ctcccgtatc gtagttatct acacgacggg    3540
gagtcaggca actatggatg aacgaaatag acagatcgct gagataggtg cctcactgat    3600
taagcattgg taactgtcag accaagttta ctcatatata ctttagattg atttaaaact    3660 tcattttaa tttaaaagga tctaggtgaa gatcctttt gataatctca tgaccaaaat    3720
cccttaacgt gagttttcgt tccactgagc gtcagacccc gtagaaaaga tcaaaggatc    3780
ttcttgagat ccttttttc tgcgcgtaat ctgctgcttg caacaaaaa accaccgct    3840 accagcggtg gtttgtttgc cggatcaaga gctaccaact ctttttccga aggtaactgg    3900
cttcagcaga gcgcagatac caaatactgt ccttctagtg tagccgtagt taggccacca    3960
cttcaagaac tctgtagcac cgcctacata cctcgctctg ctaatcctgt taccagtggc    4020
```

```
tgctgccagt ggcgataagt cgtgtcttac cgggttggac tcaagacgat agttaccgga   4080
taaggcgcag cggtcgggct gaacgggggg ttcgtgcaca cagcccagct tggagcgaac   4140
gacctacacc gaactgagat acctacagcg tgagcattga gaaagcgcca cgcttcccga   4200
agggagaaag gcggacaggt atccggtaag cggcagggtc ggaacaggag agcgcacgag   4260
ggagcttcca gggggaaacg cctggtatct ttatagtcct gtcgggtttc gccacctctg   4320
acttgagcgt cgattttgt gatgctcgtc agggggcgg agcctatgga aaacgccag     4380 caacgcggcc ttttacggt tcctggcctt ttgctggcct tttgctcaca tgttctttcc    4440
tgcgttatcc cctgattctg tggataaccg tattaccgcc tttgagtgag ctgataccgc   4500
tcgccgcagc cgaacgaccg agcgcagcga gtcagtgagc gaggaagcgg aagagcgccc   4560
aatacgcaaa ccgcctctcc ccgcgcgttg gccgattcat taatgcagag cttgcaattc   4620
gcgcgttttt caatattatt gaagcattta tcagggttat tgtctcatga gcggatacat   4680
atttgaatgt atttagaaaa ataaacaaat aggggttccg cgcacatttc cccgaaaagt   4740
gccacctgac gtctaagaaa ccattattat catgacatta acctataaaa ataggcgtag   4800
tacgaggccc tttcactcat tagatgcatg tcgttacata acttacggta aatgccccgc   4860
ctggctgacc gcccaacgac ccccgcccat tgacgtcaat aatgacgtat gttcccatag   4920
taacgccaat agggactttc cattgacgtc aatgggtgga gtatttacgg taaactgccc   4980
acttggcagt acatcaagtg tatcatatgc caagtacgcc ccctattgac gtcaatgacg   5040
gtaaatggcc cgcctggcat tatgcccagt acatgacctt atgggacttt cctacttggc   5100
agtacatcta cgtattagtc atcgctatta ccatggtgat gcggttttgg cagtacatca   5160
atgggcgtgg atagcggttt gactcacggg gatttccaag tctccacccc attgacgtca   5220
atgggagttt gttttggcac caaaatcaac gggactttcc aaaatgtcgt aacaactccg   5280
ccccattgac gcaaatgggc ggtaggcgtg tacggtggga ggtctatata agcagagctc   5340
gtttagtgaa ccgtcagatc gcctggagac gccatccacg ctgttttgac ctccatagaa   5400
gacaccggga ccgatccagc ctccggactc tagcctaggc gcggaccat gtccggcttg     5460 aacgacatct tcgaggccca agatcgag tggcacgagg aaaagcttcg aaccatggtg     5520
agcaagggcg aggagctgtt caccggggtg gtgcccatcc tggtcgagct ggacggcgac   5580
gtaaacggcc acaagttcag cgtgtccggc gagggcgagg gcgatgccac ctacggcaag   5640
ctgaccctga agttcatctg caccaccggc aagctgcccg tgccctggcc caccctcgtg   5700
accaccctga cctacggcgt gcagtgcttc agccgctacc ccgaccacat gaagcagcac   5760
gacttcttca gtccgccat gcccgaaggc tacgtccagg agcgcaccat cttcttcaag   5820
gacgacggca actacaagac ccgcgccgag gtgaagttcg agggcgacac cctggtgaac   5880
cgcatcgagc tgaagggcat cgacttcaag gaggacggca acatcctggg gcacaagctg   5940
gagtacaact acaacagcca caacgtctat atcatggccg acaagcagaa gaacggcatc   6000
aaggtgaact tcaagatccg ccacaacatc gaggacggca gcgtgcagct cgccgaccac   6060
taccagcaga acacccccat cggcgacggc cccgtgctgc tgcccgacaa ccactacctg   6120
agcacccagt ccgccctgag caaagacccc aacgagaagc gcgatcacat ggtcctgctg   6180
gagttcgtga ccgccgccgg gatcactctc ggcatggacg agctgtacaa gtagctcgag   6240
tgcggcccca ataatgatt ttattttgac tgatagtgac ctgttcgttg caacaaattg    6300
atgagcaatg ctttttttata atgccaactt tgtacaaaaa agcaggctgc gatcgctcgg   6360
```

-continued

| | |
|---|---|
| gcaggaagag ggcctatttc ccatgattcc ttcatatttg catatacgat acaaggctgt | 6420 |
| tagagagata attagaatta atttgactgt aaacacaaag atattagtac aaaatacgtg | 6480 |
| acgtagaaag taataatttc ttgggtagtt tgcagtttta aaattatgtt ttaaaatgga | 6540 |
| ctatcatatg cttaccgtaa cttgaaagta tttcgatttc ttgggtttat atatcttgtg | 6600 |
| gaaaggacga ggatccggga gatttgttaa tgataccatc aagagtggta tcattaacaa | 6660 |
| atctcctttt ttg | 6673 |

<210> SEQ ID NO 8
<211> LENGTH: 6673
<212> TYPE: DNA
<213> ORGANISM: Artificial Sequence
<220> FEATURE:
<223> OTHER INFORMATION: human shTACE #2 vector

<400> SEQUENCE: 8

| | |
|---|---|
| gaattcgcgg ccctagcttg ggatctttgt gaaggaacct tacttctgtg gtgtgacata | 60 |
| attggacaaa ctacctacag agatttaaag ctctaaggta aatataaaat ttttaagtgt | 120 |
| ataatgtgtt aaactagctg catatgcttg ctgcttgaga gttttgctta ctgagtatga | 180 |
| tttatgaaaa tattatacac aggagctagt gattctaatt gttgtgtat tttagattca | 240 |
| cagtcccaag gctcatttca ggcccctcag tcctcacagt ctgttcatga tcataatcag | 300 |
| ccataccaca tttgtagagg ttttacttgc tttaaaaaac ctcccacacc tccccctgaa | 360 |
| cctgaaacat aaaatgaatg caattgttgt tgttaacttg tttattgcag cttataatgg | 420 |
| ttacaaataa agcaatagca tcacaaattt cacaaataaa gcatttttt cactgcattc | 480 |
| tagttgtggt ttgtccaaac tcatcaatgt atcttatcat gtctggatcg atcctgcatt | 540 |
| aatgaatcgg ccaacgcgcg gggagaggcg gtttgcgtat tggctggcgt aatagcgaag | 600 |
| aggcccgcac cgatcgccct tcccaacagt tgcgcagcct gaatggcgaa tgggacgcgc | 660 |
| cctgtagcgg cgcattaagc gcggcgggtg tggtggttac gcgcagcgtg accgctacac | 720 |
| ttgccagcgc cctagcgccc gctcctttcg ctttcttccc ttcctttctc gccacgttcg | 780 |
| ccggctttcc ccgtcaagct ctaaatcggg gctccctttt agggttccga tttagtgctt | 840 |
| tacggcacct cgaccccaaa aaacttgatt agggtgatgg ttcacgtagt gggccatcgc | 900 |
| cctgatagac ggttttttcgc cctttgacgt tggagtccac gttctttaat agtggactct | 960 |
| tgttccaaac tggaacaaca ctcaacccta tctcggtcta ttcttttgat ttataaggga | 1020 |
| ttttgccgat ttcggcctat tggttaaaaa atgagctgat ttaacaaata tttaacgcga | 1080 |
| attttaacaa aatattaacg tttacaattt cgcctgatgc ggtattttct ccttacgcat | 1140 |
| ctgtgcggta tttcacaccg catacgcgga tctgcgcagc accatggcct gaaataacct | 1200 |
| ctgaaagagg aacttggtta ggaaccttct gaggcggaaa gaaccagctg tggaatgtgt | 1260 |
| gtcagttagg gtgtggaaag tccccaggct ccccagcagg cagaagtatg caaagcatgc | 1320 |
| atctcaatta gtcagcaacc aggtgtggaa agtccccagg ctccccagca ggcagaagta | 1380 |
| tgcaaagcat gcatctcaat tagtcagcaa ccatagtccc gcccctaact ccgcccatcc | 1440 |
| cgcccctaac tccgcccagt tccgcccatt ctccgcccca tggctgacta atttttttta | 1500 |
| tttatgcaga ggccgaggcc gcctcggcct ctgagctatt ccagaagtag tgaggaggct | 1560 |
| ttttttggagg cctaggcttt tgcaaaaagc ttgattcttc tgacacaaca gtctcgaact | 1620 |
| taaggctaga gccaccatga ccgagtacaa gcccacggtg cgcctcgcca ccgcgacga | 1680 |
| cgtccccagg gccgtacgca ccctcgccgc cgcgttcgcc gactaccccg ccacgcgcca | 1740 |

```
caccgtcgat ccggaccgcc acatcgagcg ggtcaccgag ctgcaagaac tcttcctcac    1800
gcgcgtcggg ctcgacatcg gcaaggtgtg ggtcgcggac gacggcgccg cggtggcggt    1860
ctggaccacg ccggagagcg tcgaagcggg ggcggtgttc gccgagatcg gcccgcgcat    1920
ggccgagttg agcggttccc ggctggccgc gcagcaacag atggaaggcc tcctggcgcc    1980
gcaccggccc aaggagcccg cgtggttcct ggccaccgtc ggcgtctcgc ccgaccacca    2040
gggcaagggt ctgggcagcg ccgtcgtgct ccccggagtg gaggcggccg agcgcgccgg    2100
ggtgcccgcc ttcctggaga cctccgcgcc ccgcaacctc cccttctacg agcggctcgg    2160
cttcaccgtc accgccgacg tcgaggtgcc cgaaggaccg cgaacctggt gcatgacccg    2220
caagcccggt gcctgagttt aacgaaatga ccgaccaagc gacgcccaac ctgccatcac    2280
gatggccgca ataaaatatc tttattttca ttacatctgt gtgttggttt tttgtgtgga    2340
tcgatagcga taaggatcga tccgcgcatg gtgcactctc agtacaatct gctctgatgc    2400
cgcatagtta agccagcccc gacacccgcc aacacccgct gacgcgccct gacgggcttg    2460
tctgctcccg gcatccgctt acagacaagc tgtgaccgtc tccgggagct gcatgtgtca    2520
gaggttttca ccgtcatcac cgaaacgcgc gagacgaaag gcctcgtgat acgcctatt     2580 tttataggtt aatgtcatga taataatggt ttcttagacg tcaggtggca cttttcgggg    2640
aaatgtgcgc ggaacccta tttgtttatt tttctaaata cattcaaata tgtatccgct      2700
catgagacaa taaccctgat aaatgcttca ataatattga aaaggaaga gtatgagtat       2760 tcaacatttc cgtgtcgccc ttattcccctt ttttgcggca ttttgccttc ctgttttttgc    2820 tcacccagaa acgctggtga agtaaaaga tgctgaagat cagttgggtg cacgagtggg     2880
ttacatcgaa ctggatctca acagcggtaa gatccttgag agttttcgcc ccgaagaccg    2940
ttttccaatg atgagcactt ttaaagttct gctatgtggc gcggtattat cccgtattga    3000
cgccgggcaa gagcaactcg gtcgccgcat acactattct cagaatgact tggttgagta    3060
ctcaccagtc acagaaaagc atcttacgga tggcatgaca gtaagagaat tatgcagtgc    3120
tgccataacc atgagtgata acactgcggc caacttactt ctgacaacga tcggaggacc    3180
gaaggagcta accgcttttt tgcacaacat gggggatcat gtaactcgcc ttgatcgttg    3240
ggaaccggag ctgaatgaag ccataccaaa cgacgagcgt gacaccacga tgcctgtagc    3300
aatggcaaca acgttgcgca aactattaac tggcgaacta cttactctag cttcccggca    3360
acaattaata gactggatgg aggcggataa agttgcagga ccacttctgc gctcggccct    3420
tccggctggc tggtttattg ctgataaatc tggagccggt gagcgtgggt ctcgcggtat    3480
cattgcagca ctggggccag atggtaagcc ctcccgtatc gtagttatct acacgacggg    3540
gagtcaggca actatggatg aacgaaatag acagatcgct gagataggtg cctcactgat    3600
taagcattgg taactgtcag accaagttta ctcatatata ctttagattg atttaaaact    3660 tcattttta tttaaaagga tctaggtgaa gatcctttttt gataatctca tgaccaaaat    3720
cccttaacgt gagttttcgt tccactgagc gtcagacccc gtagaaaaga tcaaaggatc    3780
ttcttgagat cctttttttc tgcgcgtaat ctgctgcttg caaacaaaaa aaccaccgct    3840
accagcggtg gtttgtttgc cggatcaaga gctaccaact ctttttccga aggtaactgg    3900
cttcagcaga gcgcagatac caaatactgt ccttctagtg tagccgtagt taggccacca    3960
cttcaagaac tctgtagcac cgcctacata cctcgctctg ctaatcctgt taccagtggc    4020
tgctgccagt ggcgataagt cgtgtcttac cgggttggac tcaagacgat agttaccgga    4080
```

```
taaggcgcag cggtcgggct gaacggggg ttcgtgcaca cagcccagct ggagcgaac    4140 gacctacacc gaactgagat acctacagcg tgagcattga gaaagcgcca cgcttcccga    4200
agggagaaag gcggacaggt atccggtaag cggcagggtc ggaacaggag agcgcacgag    4260
ggagcttcca gggggaaacg cctggtatct ttatagtcct gtcgggtttc gccacctctg    4320
acttgagcgt cgattttgt gatgctcgtc aggggggcgg agcctatgga aaaacgccag    4380
caacgcggcc tttttacggt tcctggcctt ttgctggcct tttgctcaca tgttctttcc    4440
tgcgttatcc cctgattctg tggataaccg tattaccgcc tttgagtgag ctgataccgc    4500
tcgccgcagc cgaacgaccg agcgcagcga gtcagtgagc gaggaagcgg aagagcgccc    4560
aatacgcaaa ccgcctctcc ccgcgcgttg gccgattcat taatgcagag cttgcaattc    4620
gcgcgttttt caatattatt gaagcattta tcagggttat tgtctcatga gcggatacat    4680
atttgaatgt atttagaaaa ataaacaaat aggggttccg cgcacatttc cccgaaaagt    4740
gccacctgac gtctaagaaa ccattattat catgacatta acctataaaa ataggcgtag    4800
tacgaggccc tttcactcat tagatgcatg tcgttacata acttacggta aatggcccgc    4860
ctggctgacc gcccaacgac ccccgcccat tgacgtcaat aatgacgtat gttcccatag    4920
taacgccaat agggactttc cattgacgtc aatgggtgga gtatttacgg taaactgccc    4980
acttggcagt acatcaagtg tatcatatgc caagtacgcc ccctattgac gtcaatgacg    5040
gtaaatggcc cgcctggcat tatgcccagt acatgacctt atgggacttt cctacttggc    5100
agtacatcta cgtattagtc atcgctatta ccatggtgat gcggttttgg cagtacatca    5160
atgggcgtgg atagcggttt gactcacggg gatttccaag tctccacccc attgacgtca    5220
atgggagttt gttttggcac caaaatcaac gggactttcc aaaatgtcgt aacaactccg    5280
ccccattgac gcaaatgggc ggtaggcgtg tacggtggga ggtctatata agcagagctc    5340
gtttagtgaa ccgtcagatc gcctggagac gccatccacg ctgttttgac ctccatagaa    5400
gacaccggga ccgatccagc ctccggactc tagcctaggc gcggaccat gtccggcttg    5460 aacgacatct tcgaggccca aagatcgag tggcacgagg aaaagcttcg aaccatggtg    5520
agcaagggcg aggagctgtt caccggggtg gtgcccatcc tggtcgagct ggacggcgac    5580
gtaaacggcc acaagttcag cgtgtccggc gagggcgagg gcgatgccac ctacggcaag    5640
ctgaccctga agttcatctg caccaccggc aagctgcccg tgccctggcc caccctcgtg    5700
accaccctga cctacggcgt gcagtgcttc agccgctacc ccgaccacat gaagcagcac    5760
gacttcttca gtccgccat gcccgaaggc tacgtccagg agcgcaccat cttcttcaag    5820
gacgacggca actacaagac ccgcgccgag gtgaagttcg agggcgacac cctggtgaac    5880
cgcatcgagc tgaagggcat cgacttcaag gaggacggca acatcctggg gcacaagctg    5940
gagtacaact acaacagcca caacgtctat atcatggccg acaagcagaa gaacggcatc    6000
aaggtgaact tcaagatccg ccacaacatc gaggacggca gcgtgcagct cgccgaccac    6060
taccagcaga acaccccat cggcgacggc cccgtgctgc tgcccgacaa ccactacctg    6120
agcacccagt ccgccctgag caaagacccc aacgagaagc gcgatcacat ggtcctgctg    6180
gagttcgtga ccgccgccgg gatcactctc ggcatggacg agctgtacaa gtagctcgag    6240
tgcggcccca ataatgatt ttattttgac tgatagtgac ctgttcgttg caacaaattg    6300
atgagcaatg cttttttata tgccaactt tgtacaaaaa agcaggctgc gatcgctcgg    6360
gcaggaagag ggcctatttc ccatgattcc ttcatatttg catatacgat acaaggctgt    6420
tagagagata attagaatta atttgactgt aaacacaaag atattagtac aaaatacgtg    6480
```

```
acgtagaaag taataatttc ttgggtagtt tgcagttta aaattatgtt ttaaaatgga    6540
ctatcatatg cttaccgtaa cttgaaagta tttcgatttc ttgggttat atatcttgtg    6600 gaaaggacga ggatccgcct ggttacaact catgaatttc aagagaattc atgagttgta    6660
accaggtttt ttg                                                      6673

<210> SEQ ID NO 9
<211> LENGTH: 6673
<212> TYPE: DNA
<213> ORGANISM: Artificial Sequence
<220> FEATURE:
<223> OTHER INFORMATION: human shTACE #3 vector

<400> SEQUENCE: 9
gaattcgcgg ccctagcttg ggatctttgt gaaggaacct tacttctgtg gtgtgacata      60
attggacaaa ctacctacag agatttaaag ctctaaggta aatataaaat ttttaagtgt     120
ataatgtgtt aaactagctg catatgcttg ctgcttgaga gttttgctta ctgagtatga     180
tttatgaaaa tattatacac aggagctagt gattctaatt gtttgtgtat tttagattca     240
cagtcccaag gctcatttca ggcccctcag tcctcacagt ctgttcatga tcataatcag     300
ccataccaca tttgtagagg ttttacttgc tttaaaaaac ctcccacacc tccccctgaa     360
cctgaaacat aaaatgaatg caattgttgt tgttaacttg tttattgcag cttataatgg     420
ttacaaataa agcaatagca tcacaaattt cacaaataaa gcattttttt cactgcattc     480
tagttgtggt ttgtccaaac tcatcaatgt atcttatcat gtctggatcg atcctgcatt     540
aatgaatcgg ccaacgcgcg gggagaggcg gtttgcgtat tggctggcgt aatagcgaag     600
aggcccgcac cgatcgccct tcccaacagt tgcgcagcct gaatggcgaa tgggacgcgc     660
cctgtagcgg cgcattaagc gcggcgggtg tggtggttac gcgcagcgtg accgctacac     720
ttgccagcgc cctagcgccc gctccttcg ctttcttccc ttcctttctc gccacgttcg     780
ccggctttcc ccgtcaagct ctaaatcggg ggctcccttt agggttccga tttagtgctt     840
tacggcacct cgaccccaaa aaacttgatt agggtgatgg ttcacgtagt gggccatcgc     900
cctgatagac ggttttcgc cctttgacgt tggagtccac gttctttaat agtggactct     960
tgttccaaac tggaacaaca ctcaacccta tctcggtcta ttcttttgat ttataaggga    1020
ttttgccgat ttcggcctat tggttaaaaa atgagctgat ttaacaaata tttaacgcga    1080
attttaacaa aatattaacg tttacaattt cgcctgatgc ggtattttct ccttacgcat    1140
ctgtgcggta tttcacaccg catacgcgga tctgcgcagc accatggcct gaaataacct    1200
ctgaaagagg aacttggtta ggaaccttct gaggcggaaa gaaccagctg tggaatgtgt    1260
gtcagttagg gtgtggaaag tccccaggct cccagcagg cagaagtatg caaagcatgc    1320
atctcaatta gtcagcaacc aggtgtggaa agtccccagg ctccccagca ggcagaagta    1380
tgcaaagcat gcatctcaat tagtcagcaa ccatagtccc gcccctaact ccgcccatcc    1440
cgcccctaac tccgcccagt tccgcccatt ctccgcccca tggctgacta attttttta    1500 tttatgcaga ggccgaggcc gcctcggcct ctgagctatt ccagaagtag tgaggaggct    1560
tttttggagg cctaggcttt tgcaaaaagc ttgattcttc tgacacaaca gtctcgaact    1620
taaggctaga gccaccatga ccgagtacaa gcccacggtg cgcctcgcca cccgcgacga    1680
cgtccccagg gccgtacgca ccctcgccgc cgcgttcgcc gactaccccg ccacgcgcca    1740
caccgtcgat ccggaccgcc acatcgagcg ggtcaccgag ctgcaagaac tcttcctcac    1800
```

-continued

```
gcgcgtcggg ctcgacatcg gcaaggtgtg ggtcgcggac gacggcgccg cggtggcggt    1860
ctggaccacg ccggagagcg tcgaagcggg ggcggtgttc gccgagatcg gcccgcgcat    1920
ggccgagttg agcggttccc ggctggccgc gcagcaacag atggaaggcc tcctggcgcc    1980
gcaccggccc aaggagcccg cgtggttcct ggccaccgtc ggcgtctcgc ccgaccacca    2040
gggcaagggt ctgggcagcg ccgtcgtgct ccccggagtg gaggcggccg agcgcgccgg    2100
ggtgcccgcc ttcctggaga cctccgcgcc ccgcaacctc cccttctacg agcggctcgg    2160
cttcaccgtc accgccgacg tcgaggtgcc cgaaggaccg cgaacctggt gcatgacccg    2220
caagcccggt gcctgagttt aacgaaatga ccgaccaagc gacgcccaac ctgccatcac    2280
gatggccgca ataaaatatc tttattttca ttacatctgt gtgttggttt tttgtgtgga    2340
tcgatagcga taaggatcga tccgcgcatg gtgcactctc agtacaatct gctctgatgc    2400
cgcatagtta agccagcccc gacacccgcc aacacccgct gacgcgccct gacgggcttg    2460
tctgctcccg gcatccgctt acagacaagc tgtgaccgtc tccgggagct gcatgtgtca    2520
gaggttttca ccgtcatcac cgaaacgcgc gagacgaaag ggcctcgtga tacgcctatt    2580
tttataggtt aatgtcatga taataatggt ttcttagacg tcaggtggca cttttcgggg    2640
aaaatgtgcgc ggaaccccta tttgtttatt tttctaaata cattcaaata tgtatccgct    2700
catgagacaa taaccctgat aaatgcttca ataatattga aaaggaagag gtatgagtat    2760
tcaacatttc cgtgtcgccc ttattccctt ttttgcggca ttttgccttc ctgttttgc    2820
tcacccagaa acgctggtga agtaaaaga tgctgaagat cagttgggtg cacgagtggg    2880
ttacatcgaa ctggatctca acagcggtaa gatccttgag agttttcgcc ccgaagaccg    2940
ttttccaatg atgagcactt ttaaagttct gctatgtggc gcggtattat cccgtattga    3000
cgccgggcaa gagcaactcg gtcgccgcat acactattct cagaatgact tggttgagta    3060
ctcaccagtc acagaaaagc atcttacgga tggcatgaca gtaagagaat tatgcagtgc    3120
tgccataacc atgagtgata acactgcggc caacttactt ctgacaacga tcggaggacc    3180
gaaggagcta accgcttttt tgcacaacat gggggatcat gtaactcgcc ttgatcgttg    3240
ggaaccggag ctgaatgaag ccataccaaa cgacgagcgt gacaccacga tgcctgtagc    3300
aatggcaaca acgttgcgca aactattaac tggcgaacta cttactctag cttcccggca    3360
acaattaata gactggatgg aggcggataa agttgcagga ccacttctgc gctcggccct    3420
tccggctggc tggtttattg ctgataaatc tggagccggt gagcgtgggt ctcgcggtat    3480
cattgcagca ctggggccag atggtaagcc ctcccgtatc gtagttatct acacgacggg    3540
gagtcaggca actatggatg aacgaaatag acagatcgct gagataggtg cctcactgat    3600
taagcattgg taactgtcag accaagttta ctcatatata ctttagattg atttaaaact    3660
tcatttttaa tttaaaagga tctaggtgaa gatcctttt gataatctca tgaccaaaat    3720
cccttaacgt gagttttcgt tccactgagc gtcagacccc gtagaaaaga tcaaaggatc    3780
ttcttgagat cctttttttc tgcgcgtaat ctgctgcttg caaacaaaaa aaccaccgct    3840
accagcggtg gtttgtttgc cggatcaaga gctaccaact cttttttccga aggtaactgg    3900
cttcagcaga gcgcagatac caaatactgt ccttctagtg tagccgtagt taggccacca    3960
cttcaagaac tctgtagcac cgcctacata cctcgctctg ctaatcctgt taccagtggc    4020
tgctgccagt ggcgataagt cgtgtcttac cgggttggac tcaagacgat agttaccgga    4080
taaggcgcag cggtcgggct gaacggggg ttcgtgcaca cagcccagct tggagcgaac    4140
gacctacacc gaactgagat acctacagcg tgagcattga gaaagcgcca cgcttcccga    4200
```

```
agggagaaag gcggacaggt atccggtaag cggcagggtc ggaacaggag agcgcacgag   4260
ggagcttcca gggggaaacg cctggtatct ttatagtcct gtcgggtttc gccacctctg   4320
acttgagcgt cgattttgt gatgctcgtc agggggcgg agcctatgga aaaacgccag    4380
caacgcggcc tttttacggt tcctggcctt ttgctggcct tttgctcaca tgttctttcc   4440
tgcgttatcc cctgattctg tggataaccg tattaccgcc tttgagtgag ctgataccgc   4500
tcgccgcagc cgaacgaccg agcgcagcga gtcagtgagc gaggaagcgg aagagcgccc   4560
aatacgcaaa ccgcctctcc ccgcgcgttg gccgattcat taatgcagag cttgcaattc   4620
gcgcgttttt caatattatt gaagcattta tcagggttat tgtctcatga gcggatacat   4680
atttgaatgt atttagaaaa ataaacaaat aggggttccg cgcacatttc cccgaaaagt   4740
gccacctgac gtctaagaaa ccattattat catgacatta acctataaaa ataggcgtag   4800
tacgaggccc tttcactcat tagatgcatg tcgttacata acttacggta aatggcccgc   4860
ctggctgacc gcccaacgac ccccgcccat tgacgtcaat aatgacgtat gttcccatag   4920
taacgccaat agggactttc cattgacgtc aatgggtgga gtatttacgg taaactgccc   4980
acttggcagt acatcaagtg tatcatatgc caagtacgcc ccctattgac gtcaatgacg   5040
gtaaatggcc cgcctggcat tatgcccagt acatgacctt atgggacttt cctacttggc   5100
agtacatcta cgtattagtc atcgctatta ccatggtgat gcggttttgg cagtacatca   5160
atgggcgtgg atagcggttt gactcacggg gatttccaag tctccacccc attgacgtca   5220
atgggagttt gttttggcac caaaatcaac gggactttcc aaaatgtcgt aacaactccg   5280
ccccattgac gcaaatgggc ggtaggcgtg tacggtggga ggtctatata agcagagctc   5340
gtttagtgaa ccgtcagatc gcctggagac gccatccacg ctgttttgac ctccatagaa   5400
gacaccggga ccgatccagc ctccggactc tagcctaggc gcggaccat gtccggcttg    5460 aacgacatct tcgaggccca gaagatcgag tggcacgagg aaaagcttcg aaccatggtg   5520
agcaagggcg aggagctgtt caccggggtg gtgcccatcc tggtcgagct ggacggcgac   5580
gtaaacggcc acaagttcag cgtgtccggc gagggcgagg gcgatgccac ctacggcaag   5640
ctgaccctga agttcatctg caccaccggc aagctgcccg tgcccctggcc cacccctcgtg   5700 accaccctga cctacggcgt gcagtgcttc agccgctacc ccgaccacat gaagcagcac   5760
gacttcttca agtccgccat gcccgaaggc tacgtccagg agcgcaccat cttcttcaag   5820
gacgacggca actacaagac ccgcgccgag gtgaagttcg agggcgacac cctggtgaac   5880
cgcatcgagc tgaagggcat cgacttcaag gaggacggca acatcctggg gcacaagctg   5940
gagtacaact acaacagcca caacgtctat atcatggccg acaagcagaa gaacggcatc   6000
aaggtgaact tcaagatccg ccacaacatc gaggacggca gcgtgcagct cgccgaccac   6060
taccagcaga acacccccat cggcgacggc cccgtgctgc tgcccgacaa ccactacctg   6120
agcacccagt ccgccctgag caaagacccc aacgagaagc gcgatcacat ggtcctgctg   6180
gagttcgtga ccgccgccgg gatcactctc ggcatggacg agctgtacaa gtagctcgag   6240
tgcggcccca ataatgatt ttatttgac tgatagtgac ctgttcgttg caacaaattg    6300
atgagcaatg cttttttata tgccaactt tgtacaaaaa agcaggctgc gatcgctcgg    6360
gcaggaagag ggcctatttc ccatgattcc ttcatatttg catatacgat acaaggctgt   6420
tagagagata attagaatta atttgactgt aaacacaaag atattagtac aaaatacgtg   6480
acgtagaaag taataatttc ttgggtagtt tgcagtttta aaattatgtt ttaaaatgga   6540
```

```
ctatcatatg cttaccgtaa cttgaaagta tttcgatttc ttgggtttat atatcttgtg    6600
gaaaggacga ggatccgggc gattaatgct acttgcaatc aagagttgca agtagcatta    6660
atcgcctttt ttg                                                       6673

<210> SEQ ID NO 10
<211> LENGTH: 6673
<212> TYPE: DNA
<213> ORGANISM: Artificial Sequence
<220> FEATURE:
<223> OTHER INFORMATION: human shTACE #4 vector

<400> SEQUENCE: 10
gaattcgcgg ccctagcttg ggatctttgt gaaggaacct tacttctgtg gtgtgacata      60
attggacaaa ctacctacag agatttaaag ctctaaggta aatataaaat ttttaagtgt     120
ataatgtgtt aaactagctg catatgcttg ctgcttgaga gttttgctta ctgagtatga     180
tttatgaaaa tattatacac aggagctagt gattctaatt gtttgtgtat tttagattca     240
cagtcccaag gctcatttca ggcccctcag tcctcacagt ctgttcatga tcataatcag     300
ccataccaca tttgtagagg ttttacttgc tttaaaaaac ctcccacacc tccccctgaa     360
cctgaaacat aaaatgaatg caattgttgt tgttaacttg tttattgcag cttataatgg     420
ttacaaataa agcaatagca tcacaaattt cacaaataaa gcattttttt cactgcattc     480
tagttgtggt ttgtccaaac tcatcaatgt atcttatcat gtctggatcg atcctgcatt     540
aatgaatcgg ccaacgcgcg gggagaggcg gtttgcgtat tggctggcgt aatagcgaag     600
aggcccgcac cgatcgccct tcccaacagt tgcgcagcct gaatggcgaa tgggacgcgc     660
cctgtagcgg cgcattaagc gcggcgggtg tggtggttac gcgcagcgtg accgctacac     720
ttgccagcgc cctagcgccc gctcctttcg ctttcttccc ttcctttctc gccacgttcg     780
ccggctttcc ccgtcaagct ctaaatcggg ggctcccttt agggttccga tttagtgctt     840
tacggcacct cgaccccaaa aaacttgatt agggtgatgg ttcacgtagt gggccatcgc     900
cctgatagac ggtttttcgc cctttgacgt tggagtccac gttctttaat agtggactct     960
tgttccaaac tggaacaaca ctcaacccta tctcggtcta ttcttttgat ttataaggga    1020
ttttgccgat ttcggcctat tggttaaaaa atgagctgat ttaacaaata tttaacgcga    1080
attttaacaa aatattaacg tttacaattt cgcctgatgc ggtattttct ccttacgcat    1140
ctgtgcggta tttcacaccg catacgcgga tctgcgcagc accatggcct gaaataacct    1200
ctgaaagagg aacttggtta ggaaccttct gaggcgaaaa gaaccagctg tggaatgtgt    1260
gtcagttagg gtgtggaaag tccccaggct ccccagcagg cagaagtatg caaagcatgc    1320
atctcaatta gtcagcaacc aggtgtggaa agtcccaggc tccccagcag gcagaagta    1380 tgcaaagcat gcatctcaat tagtcagcaa ccatagtccc gcccctaact ccgcccatcc    1440
cgcccctaac tccgcccagt tccgcccatt ctccgcccca tggctgacta attttttta    1500 tttatgcaga ggccgaggcc gcctcggcct ctgagctatt ccagaagtag tgaggaggct    1560 ttttggagg cctaggcttt tgcaaaaagc ttgattcttc tgacacaaca gtctcgaact    1620
taaggctaga gccaccatga ccgagtacaa gcccacggtg cgcctcgcca cccgcgacga    1680
cgtccccagg gccgtacgca ccctcgccgc cgcgttcgcc gactaccccg ccacgcgcca    1740
caccgtcgat ccggaccgcc acatcgagcg ggtcaccgag ctgcaagaac tcttcctcac    1800
gcgcgtcggt ctcgacatcg gcaaggtgtg ggtcgcggac gacggcgccg cggtggcggt    1860
ctggaccacg ccggagagcg tcgaagcggg ggcggtgttc gccgagatcg gcccgcgcat    1920
```

```
ggccgagttg agcggttccc ggctggccgc gcagcaacag atggaaggcc tcctggcgcc   1980
gcaccggccc aaggagcccg cgtggttcct ggccaccgtc ggcgtctcgc ccgaccacca   2040
gggcaagggt ctgggcagcg ccgtcgtgct ccccggagtg gaggcggccg agcgcgccgg   2100
ggtgccgcc ttcctggaga cctccgcgcc ccgcaacctc cccttctacg agcggctcgg    2160
cttcaccgtc accgccgacg tcgaggtgcc cgaaggaccg cgaacctggt gcatgacccg   2220
caagcccggt gcctgagttt aacgaaatga ccgaccaagc gacgcccaac ctgccatcac   2280
gatggccgca ataaaatatc tttattttca ttacatctgt gtgttggttt tttgtgtgga   2340
tcgatagcga taaggatcga tccgcgcatg gtgcactctc agtacaatct gctctgatgc   2400
cgcatagtta agccagcccc gacacccgcc aacacccgct gacgcgccct gacgggcttg   2460
tctgctcccg gcatccgctt acagacaagc tgtgaccgtc tccgggagct gcatgtgtca   2520
gaggttttca ccgtcatcac cgaaacgcgc gagacgaaag ggcctcgtga tacgcctatt   2580
tttataggtt aatgtcatga taataatggt tccttagacg tcaggtggca cttttcgggg   2640
aaatgtgcgc ggaaccccta tttgtttatt tttctaaata cattcaaata tgtatccgct   2700
catgagacaa taaccctgat aaatgcttca ataatattga aaaggaaga gtatgagtat    2760
tcaacatttc cgtgtcgccc ttattccctt ttttgcggca ttttgccttc ctgttttgc    2820
tcacccagaa acgctggtga agtaaaaga tgctgaagat cagttgggtg cacgagtggg   2880
ttacatcgaa ctggatctca acagcggtaa gatccttgag agttttcgcc ccgaagaccg   2940
tttccaatg atgagcactt ttaaagttct gctatgtggc gcggtattat cccgtattga    3000
cgccgggcaa gagcaactcg gtcgccgcat acactattct cagaatgact tggttgagta   3060
ctcaccagtc acagaaaagc atcttacgga tggcatgaca gtaagagaat tatgcagtgc   3120
tgccataacc atgagtgata acactgcggc caacttactt ctgacaacga tcggaggacc   3180
gaaggagcta accgcttttt tgcacaacat gggggatcat gtaactcgcc ttgatcgttg   3240
ggaaccggag ctgaatgaag ccataccaaa cgacgagcgt gacaccacga tgcctgtagc   3300
aatggcaaca acgttgcgca aactattaac tggcgaacta cttactctag cttcccggca   3360
acaattaata gactggatgg aggcggataa agttgcagga ccacttctgc gctcggccct   3420
tccggctggc tggtttattg ctgataaatc tggagccggt gagcgtgggt ctcgcggtat   3480
cattgcagca ctggggccag atggtaagcc ctcccgtatc gtagttatct acacgacggg   3540
gagtcaggca actatggatg aacgaaatag acagatcgct gagataggtg cctcactgat   3600
taagcattgg taactgtcag accaagttta ctcatatata ctttagattg atttaaaact   3660
tcatttttaa tttaaaagga tctaggtgaa gatcctttt gataatctca tgaccaaaat    3720
cccttaacgt gagttttcgt tccactgagc gtcagacccc gtagaaaaga tcaaggatc    3780
ttcttgagat cctttttttc tgcgcgtaat ctgctgcttg caaacaaaaa aaccaccgct   3840
accagcggtg gtttgtttgc cggatcaaga gctaccaact ctttttccga aggtaactgg   3900
cttcagcaga gcgcagatac caaatactgt ccttctagtg tagccgtagt taggccacca   3960
cttcaagaac tctgtagcac cgcctacata cctcgctctg ctaatcctgt taccagtggc   4020
tgctgccagt ggcgataagt cgtgtcttac cgggttggac tcaagacgat agttaccgga   4080
taaggcgcag cggtcgggct gaacggggg ttcgtgcaca cagcccagct tggagcgaac    4140
gacctacacc gaactgagat acctacagcg tgagcattga gaaagcgcca cgcttcccga   4200
agggagaaag gcggacaggt atccggtaag cggcagggtc ggaacaggag agcgcacgag   4260
```

```
ggagcttcca gggggaaacg cctggtatct ttatagtcct gtcgggtttc gccacctctg    4320
acttgagcgt cgattttgt gatgctcgtc agggggcgg agcctatgga aaaacgccag      4380
caacgcggcc ttttacggt tcctggcctt ttgctggcct tttgctcaca tgttctttcc     4440
tgcgttatcc cctgattctg tggataaccg tattaccgcc tttgagtgag ctgataccgc    4500
tcgccgcagc cgaacgaccg agcgcagcga gtcagtgagc gaggaagcgg aagagcgccc    4560
aatacgcaaa ccgcctctcc ccgcgcgttg gccgattcat taatgcagag cttgcaattc    4620
gcgcgttttt caatattatt gaagcattta tcagggttat tgtctcatga gcggatacat    4680
atttgaatgt atttagaaaa ataaacaaat aggggttccg cgcacatttc cccgaaaagt    4740
gccacctgac gtctaagaaa ccattattat catgacatta acctataaaa ataggcgtag    4800
tacgaggccc tttcactcat tagatgcatg tcgttacata acttacggta aatggcccgc    4860
ctggctgacc gcccaacgac ccccgcccat tgacgtcaat aatgacgtat gttcccatag    4920
taacgccaat agggactttc cattgacgtc aatgggtgga gtatttacgg taaactgccc    4980
acttggcagt acatcaagtg tatcatatgc caagtacgcc ccctattgac gtcaatgacg    5040
gtaaatggcc cgcctggcat tatgcccagt acatgacctt atgggacttt cctacttggc    5100
agtacatcta cgtattagtc atcgctatta ccatggtgat gcggttttgg cagtacatca    5160
atgggcgtgg atagcggttt gactcacggg gatttccaag tctccacccc attgacgtca    5220
atgggagttt gttttggcac caaaatcaac gggactttcc aaaatgtcgt aacaactccg    5280
ccccattgac gcaaatgggc ggtaggcgtg tacggtggga ggtctatata agcagagctc    5340
gtttagtgaa ccgtcagatc gcctggagac gccatccacg ctgttttgac ctccatagaa    5400
gacaccggga ccgatccagc ctccggactc tagcctaggc gcgcggaccat gtccggcttg    5460 aacgacatct tcgaggccca agatcgag tggcacgagg aaaagcttcg aaccatggtg      5520
agcaagggcg aggagctgtt caccggggtg gtgcccatcc tggtcgagct ggacggcgac    5580
gtaaacggcc acaagttcag cgtgtccggc gagggcgagg gcgatgccac ctacggcaag    5640
ctgaccctga agttcatctg caccaccggc aagctgcccg tgccctggcc caccctcgtg    5700
accaccctga cctacggcgt gcagtgcttc agccgctacc ccgaccacat gaagcagcac    5760
gacttcttca gtccgccat gcccgaaggc tacgtccagg agcgcaccat cttcttcaag    5820
gacgacggca actacaagac ccgcgccgag gtgaagttcg agggcgacac cctggtgaac    5880
cgcatcgagc tgaagggcat cgacttcaag gaggacggca acatcctggg gcacaagctg    5940
gagtacaact acaacagcca caacgtctat atcatggccg acaagcagaa gaacggcatc    6000
aaggtgaact tcaagatccg ccacaacatc gaggacggca gcgtgcagct cgccgaccac    6060
taccagcaga cacccccat cggcgacggc cccgtgctgc tgcccgacaa ccactacctg     6120
agcacccagt ccgccctgag caaagacccc aacgagaagc gcgatcacat ggtcctgctg    6180
gagttcgtga ccgccgccgg gatcactctc ggcatggacg agctgtacaa gtagctcgag    6240
tgcggcccca ataatgatt ttattttgac tgatagtgac ctgttcgttg caacaaattg     6300
atgagcaatg cttttttata atgccaactt tgtacaaaaa agcaggctgc gatcgctcgg    6360
gcaggaagag ggcctatttc ccatgattcc ttcatatttg catatacgat acaaggctgt    6420
tagagagata attagaatta atttgactgt aaacacaaag atattagtac aaaatacgtg    6480
acgtagaaag taataatttc ttgggtagtt tgcagtttta aaattatgtt ttaaatgga    6540 ctatcatatg cttaccgtaa cttgaaagta tttcgatttc ttggtttat atatcttgtg    6600 gaaaggacga ggatccgcca ttgtgtggat aagaaatttc aagagaattt cttatccaca    6660
```

```
caatggtttt ttg                                                        6673
```

<210> SEQ ID NO 11
<211> LENGTH: 11
<212> TYPE: PRT
<213> ORGANISM: Artificial Sequence
<220> FEATURE:
<223> OTHER INFORMATION: Cys-(9Arg)-Cys

<400> SEQUENCE: 11

```
Cys Arg Arg Arg Arg Arg Arg Arg Arg Arg Cys
1               5                   10
```

<210> SEQ ID NO 12
<211> LENGTH: 26
<212> TYPE: PRT
<213> ORGANISM: Artificial Sequence
<220> FEATURE:
<223> OTHER INFORMATION: Cys-(8Asp)-(16Arg)-Cys

<400> SEQUENCE: 12

```
Cys Asp Asp Asp Asp Asp Asp Asp Asp Arg Arg Arg Arg Arg Arg
1               5                   10                  15

Arg Arg Arg Arg Arg Arg Arg Arg Arg Cys
                20                  25
```

<210> SEQ ID NO 13
<211> LENGTH: 20
<212> TYPE: DNA
<213> ORGANISM: Artificial Sequence
<220> FEATURE:
<223> OTHER INFORMATION: Forward primer for TACE

<400> SEQUENCE: 13

```
gtacgtcgat gcagagcaaa                                                   20
```

<210> SEQ ID NO 14
<211> LENGTH: 20
<212> TYPE: DNA
<213> ORGANISM: Artificial Sequence
<220> FEATURE:
<223> OTHER INFORMATION: Reverse primer for TACE

<400> SEQUENCE: 14

```
aaaccagaac agacccaacg                                                   20
```

<210> SEQ ID NO 15
<211> LENGTH: 20
<212> TYPE: DNA
<213> ORGANISM: Artificial Sequence
<220> FEATURE:
<223> OTHER INFORMATION: Forward primer for TNF-alpha

<400> SEQUENCE: 15

```
tccttcagac accctcaacc                                                   20
```

<210> SEQ ID NO 16
<211> LENGTH: 20
<212> TYPE: DNA
<213> ORGANISM: Artificial Sequence
<220> FEATURE:
<223> OTHER INFORMATION: Reverse primer for TNF-alpha

<400> SEQUENCE: 16

```
cagggatcaa agctgtaggc                                                   20
```

<210> SEQ ID NO 17
<211> LENGTH: 20
<212> TYPE: DNA
<213> ORGANISM: Artificial Sequence
<220> FEATURE:
<223> OTHER INFORMATION: Forward primer for MMP-1

<400> SEQUENCE: 17
agagcagatg tggaccatgc                                               20

<210> SEQ ID NO 18
<211> LENGTH: 20
<212> TYPE: DNA
<213> ORGANISM: Artificial Sequence
<220> FEATURE:
<223> OTHER INFORMATION: Reverse primer for MMP-1

<400> SEQUENCE: 18
ttgtcccgat gatctcccct                                               20

<210> SEQ ID NO 19
<211> LENGTH: 20
<212> TYPE: DNA
<213> ORGANISM: Artificial Sequence
<220> FEATURE:
<223> OTHER INFORMATION: MMP-3 Forward primer

<400> SEQUENCE: 19
tctatggacc tccccctgac                                               20

<210> SEQ ID NO 20
<211> LENGTH: 20
<212> TYPE: DNA
<213> ORGANISM: Artificial Sequence
<220> FEATURE:
<223> OTHER INFORMATION: MMP-3 Reverse primer

<400> SEQUENCE: 20
gatttgcgcc aaaagtgcct                                               20

<210> SEQ ID NO 21
<211> LENGTH: 20
<212> TYPE: DNA
<213> ORGANISM: Artificial Sequence
<220> FEATURE:
<223> OTHER INFORMATION: TNF-Receptor Forward primer

<400> SEQUENCE: 21
tgctgtacca agtgccacaa                                               20

<210> SEQ ID NO 22
<211> LENGTH: 20
<212> TYPE: DNA
<213> ORGANISM: Artificial Sequence
<220> FEATURE:
<223> OTHER INFORMATION: TNF-Receptor Reverse primer

<400> SEQUENCE: 22
ctgaggcagt gtctgaggtg                                               20

<210> SEQ ID NO 23
<211> LENGTH: 19
<212> TYPE: DNA
<213> ORGANISM: Artificial Sequence
<220> FEATURE:

```
<223> OTHER INFORMATION: GAPDH Forward primer

<400> SEQUENCE: 23
caagatcatc agcaatgcc                                               19

<210> SEQ ID NO 24
<211> LENGTH: 20
<212> TYPE: DNA
<213> ORGANISM: Artificial Sequence
<220> FEATURE:
<223> OTHER INFORMATION: GAPDH Reverse primer

<400> SEQUENCE: 24
ctgtggtcat gagtccttcc                                              20
```